US012558369B2

(12) United States Patent
D'Andrea et al.

(10) Patent No.: US 12,558,369 B2
(45) Date of Patent: Feb. 24, 2026

(54) COMPOSITIONS AND METHODS OF TREATING FANCONI ANEMIA

(71) Applicant: Dana-Farber Cancer Institute, Inc., Boston, MA (US)

(72) Inventors: Alan D'Andrea, Winchester, MA (US); Kalindi Parmar, Arlington, MA (US); Haojian Zhang, Shrewsbury, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 184 days.

(21) Appl. No.: 18/224,384

(22) Filed: Jul. 20, 2023

(65) Prior Publication Data

US 2024/0000823 A1     Jan. 4, 2024

Related U.S. Application Data

(62) Division of application No. 15/553,905, filed as application No. PCT/US2016/019625 on Feb. 25, 2016, now Pat. No. 11,707,481.

(60) Provisional application No. 62/120,593, filed on Feb. 25, 2015.

(51) Int. Cl.
| | |
|---|---|
| *A61K 31/7088* | (2006.01) |
| *A61K 45/06* | (2006.01) |
| *C12N 15/113* | (2010.01) |

(52) U.S. Cl.
CPC .......... *A61K 31/7088* (2013.01); *A61K 45/06* (2013.01); *C12N 15/1135* (2013.01); *C12N 2310/10* (2013.01); *C12N 2310/14* (2013.01); *C12N 2310/20* (2017.05); *C12N 2310/531* (2013.01)

(58) Field of Classification Search
CPC .......... C12N 2310/14; C12N 2310/531; C12N 2310/11; A61K 39/001134
See application file for complete search history.

(56) References Cited

U.S. PATENT DOCUMENTS

| | | | |
|---|---|---|---|
| 10,526,402 B2 | 1/2020 | D'Andrea et al. | |
| 2011/0213011 A1 * | 9/2011 | Dean .................. | A61K 31/7088 536/24.5 |
| 2014/0328860 A1 | 11/2014 | Scandura et al. | |
| 2018/0051075 A1 | 2/2018 | D'Andrea et al. | |

FOREIGN PATENT DOCUMENTS

| | | | | |
|---|---|---|---|---|
| WO | WO-0043499 A2 * | 7/2000 | .......... | C12N 5/0647 |
| WO | WO-2012138223 A2 * | 10/2012 | ............. | A61P 21/00 |
| WO | WO 2014/110020 A1 | 7/2014 | | |
| WO | WO 2016/138300 A1 | 9/2016 | | |
| WO | WO 2016/138301 A1 | 9/2016 | | |

OTHER PUBLICATIONS

Zhang et al. Bone marrow failure in Fanconi Anemia from hyperactive TGFB signaling. Blood (2014) 124 (21): 356 (Year: 2014).*
Adamo, A. et al. "Preventing Nonhomologous End Joining Suppresses DNA Repair Defects of Fanconi Anemia" *Mol Cell*, 39:25-35 (2010).
Bagby Grover C., "The Role of Innate Immune Dysfunction in Inherited Bone Marrow Failure", Blood & 56th Annual Meeting of the American-Society-of-Hematology; Dec. 2014, vol. 124, No. 21.
Beerman et al., "Quiescent hematopoietic stem cells accumulate DNA damage during aging that is repaired upon entry into cell cycle," Cell Stem Cell, Jul. 3, 2014, 15(1):37-50.
Bénazet, J-D. et al. "*Smad4* is required to induce digit ray primordia and to initiate the aggregation and differentiation of chondrogenic progenitors in mouse limb buds" *Development*, 139:4250-4260 (2012).
Blank et al., "TGF-ß signaling in the control of hematopoietic stem cells, "Blood, The Journal of the American Society of Hematology, Jun. 4, 2015, 125(23):3542-50.
Brenet, F. et al. "TGFbeta restores hematopoietic homeostasis after myelosuppressive chemotherapy" *J Exp Med*, 210(3):623-639 (2013).
Budke et al., "RI-1: a chemical inhibitor of RAD51 that disrupts homologous recombination in human cells," Necleic acids research, Aug. 2, 2012, 40(15):7347-57.
Bunting, S.F. & Nussenzweig, A. "Dangerous Liaisons: Fanconi Anemia and Toxic Nonhomologous End Joining in DNA Crosslink Repair" *Mol Cell*, 39:164-166 (2010).
Ceccaldi, R. et al. "Bone Marrow Failure in Fanconi Anemia Is Triggered by an Exacerbated p53/p21 Dna Damage Response that Impairs Hematopoietic Stem and Progenitor Cells" *Cell Stem Cell*, 11:36-49 (2012).
Challen et al., "Distinct hematopoietic stems cell subtypes are differentially regulated by TGF-ß1," Cell stem cell, Mar. 5, 2010, 6(3):265-78.
Chan, K.L. et al. (2009) "Replication stress induces sister-chromatid bridging at fragile site loci in mitosis" *Nat Cell Biol*, 11:753-760, including Methods and Supplementary Material, 15 pages.
Chen Katherine et al., "Radiosensitivity of fANCD2(-/-) mouse bone marrow stromal cells is altered By Abrogation of TGF-beta Signaling", Blood. 2015, Blood & 57th Annual Meeting of the American-Society-of-Hematology, vol. 126, No. 23.
Chen Zean et al., "DNA Cross-Linking Agent Sensitivity of Fanconi Anemia (FA) Cells Is Preserved in Double Knockout (DKO) SMAD3(-/-)Fancd2(-/-) Mouse Cell Lines", Dec. 2015, Abstract.
Cron, K.R. et al. "Proteasome Inhibitors Block DNA Repair and Radiosensitize Non-Small Cell Lung Cancer" *PLoS One*, 8(9):e73710, 14 pages (2013).
Crossan, G.P. et al. (2011) "Disruption of mouse Slx4, a regulator of structure-specific nucleases, phenocopies Fanconi anemia" *Nature Genetics*, 43:147-152, including Online Methods, 2 pages.
D'andrea, Alan D. Ed—Humphries R. Keith, "Fanconi Anemia and Bone Marrow Failure", Experimental Hematology, Sep. 2015, vol. 43, No. 9, Supplement 1, p. S40.
Deans, A.J. & West, S.C. (2011) "DNA interstrand crosslink repair and cancer" *Nat Rev Cancer*, 11:467-480.
Dong et al., "Role of transforming growth factor-ß in hematologic malignancies," Blood, Jun. 15, 2006, 107(12):4589-96.

(Continued)

*Primary Examiner* — Vanessa L. Ford
*Assistant Examiner* — Sandra Carter
(74) *Attorney, Agent, or Firm* — Mueting Raasch Group

(57) ABSTRACT

The present invention provides methods of treating, preventing or delaying the onset bone marrow failure in Fanconi Anemia patients.

19 Claims, 22 Drawing Sheets

Figure 1:
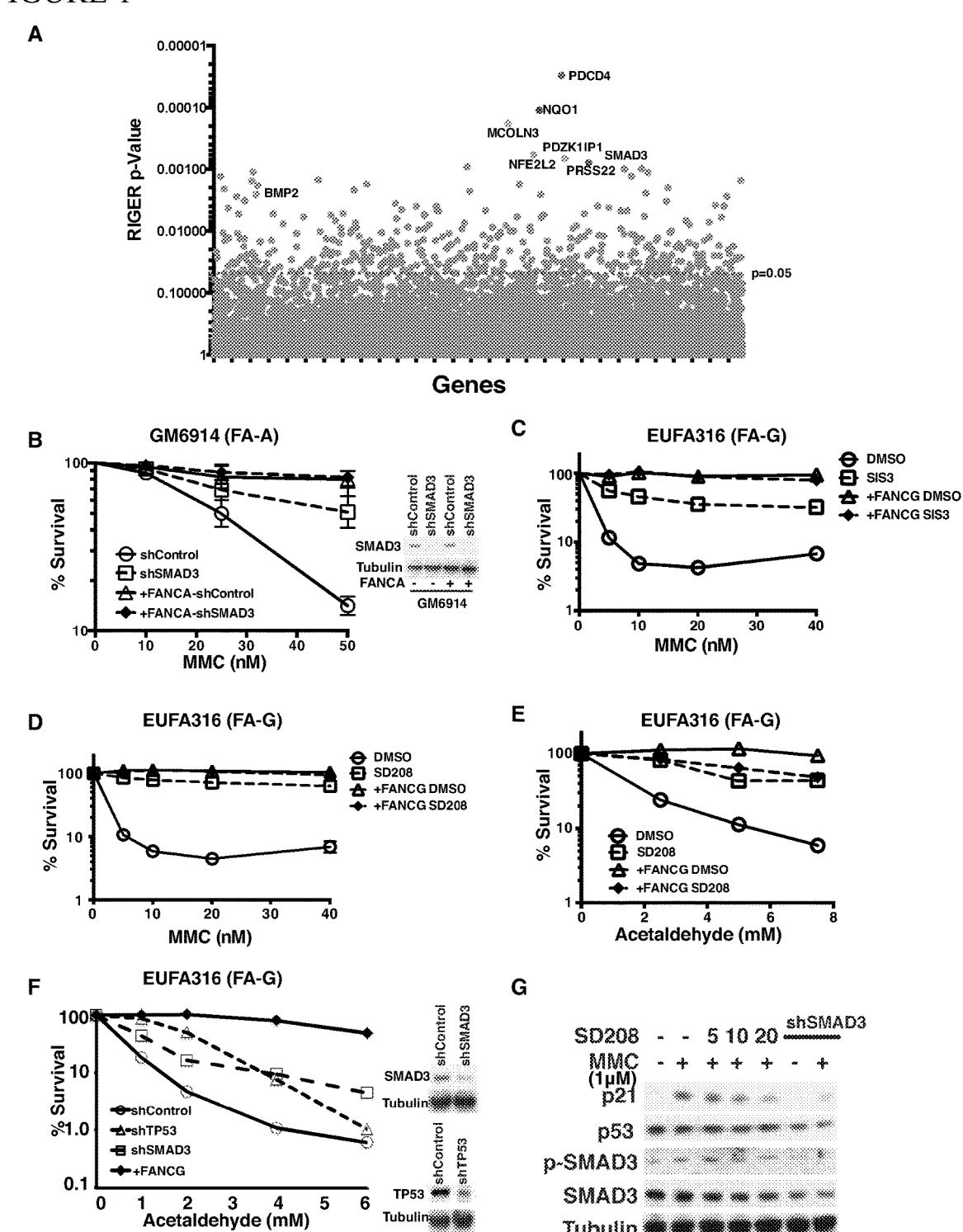

Specification includes a Sequence Listing.

(56)  References Cited

OTHER PUBLICATIONS

Dufour, C. et al. (2003) "TNF-alpha and IFN-gamma are overexpressed in the bone marrow of Fanconi anemia patients and TNF-alpha suppresses erythropoiesis in vitro" *Blood*, 102:2053-2059.

Epperly, M.W. et al. (2005) "Increased longevity of hematopoiesis in continuous bone marrow cultures and adipocytogenesis in marrow stromal cells derived from Smad3–/– mice" *Exp Hematol*, 33:353-362.

Falvello, Virginia, et al., "Production of TGF-beta Is Decreased in the Bone Marrow of Double Knockout (DKO) SMAD3(–/–) Fancd2 (–/–) Mice", Blood & 57th Annual Meeting of the American-Society-of-Hematology Dec. 2015, vol. 126, No. 23.

Garaycoechea, J.I. et al. (2012) "Genotoxic consequences of endogenous aldehydes on mouse haematopoietic stem cell function" *Nature*, 489:571-575, including Full Methods, 2 pages.

Grafe, I. et al. (2014) "Excessive transforming growth factor-beta signaling is a common mechanism in osteogenesis imperfecta" *Nature Medicine* 20:670-675, including Online Methods, 2 pages.

Hanoun, M. et al. (2014) "Acute myelogenous leukemia-induced sympathetic neuropathy promotes malignancy in an altered hematopoietic stem cell niche" *Cell Stem Cell*, 15:365-375.

Huang et al., "Inhibition of homologous recombination in human cells by targeting RAD51 recombinase," Journal of medicinal chemistry, Apr. 12, 2012, 55(7):3011-20.

Ichida, J.K. et al. (2009) "A Small-Molecule Inhibitor of Tgf-Beta Signaling Replaces *Sox2* in Reprogramming By Inducing Nanog" *Cell Stem Cell*, 5:491-503.

Ikushima, H. & Miyazono, K. (2010) "TGFbeta signalling: a complex web in cancer progression" *Nat Rev Cancer*, 10:415-424.

Ito, K. et al. (2006) "Reactive oxygen species act through p38 MAPK to limit the lifespan of hematopoietic stem cells" *Nature Medicine*, 12:446-451.

Jessen, W.J. et al. (2013) "MEK inhibition exhibits efficacy in human and mouse neurofibromatosis tumors" *J Clin Invest*, 123:340-347.

Jinnin, M. et al. (2006) "Characterization of SIS3, a novel specific inhibitor of Smad3, and its effect on transforming growth factor-betal-induced extracellular matrix expression" *Molecular Pharmacology*, 69:597-607.

Kennedy, R.D. et al. (2007) "Fanconi anemia pathway-deficient tumor cells are hypersensitive to inhibition of ataxia telangiectasia mutated" *J Clin Invest*, 117:1440-1449.

Kim et al., "Transforming growth factor-ß signaling in normal and malignant hematopoiesis," Leukemia, Sep. 2003, 17(9):1731-37.

Kirshner, J. et al. (2006) "Inhibition of transforming growth factor-betal signaling attenuates ataxia telangiectasia mutated activity in response to genotoxic stress" *Cancer Res*, 66:10861-10869.

Kottemann, M.C. & Smogorzewska, A. (2013) "Fanconi anaemia and the repair of Watson and Crick DNA crosslinks" *Nature*, 493:356-363.

Krause, D.S. et al. (2013) "Differential regulation of myeloid leukemias by the bone marrow microenvironment" *Nature Medicine*, 19:1513-1517, including Online Methods, 2 pages.

Langevin, F. et al. (2011) "Fancd2 counteracts the toxic effects of naturally produced aldehydes in mice" *Nature*, 475:53-58, including Methods, 1 page.

Li, J. et al. (2007) "TNF-alpha induces leukemic clonal evolution ex vivo in Fanconi anemia group C murine stem cells" *J Clin Invest*, 117:3283-3295.

Li, Y. et al. (2009) "Mesenchymal stem/progenitor cells promote the reconstitution of exogenous hematopoietic stem cells in *Fancg*–/– mice in vivo" *Blood*, 113:2342-2351.

Lin, T. et al. (2009) "A chemical platform for improved induction of human iPSCs" *Nat Methods*, 6:805-808.

Mansour, W.Y. et al. (2008) "Hierarchy of nonhomologous end-joining, single-strand annealing and gene conversion at site-directed DNA double-strand breaks" *Nucleic Acids Research*, 36:4088-4098.

Massaguè, "TGFß in cancer," Cell, Jul. 25, 2008, 134(2):215-30.

McKenna, D.J. et al. (2003) "Modification of the alkaline Comet assay to allow simultaneous evaluation of mitomycin C-induced DNA cross-link damage and repair of specific DNA sequences in RT4 cells" *DNA Repair* (Amst), 2:879-890.

Milyavsky, M. et al. (2010) "A distinctive DNA damage response in human hematopoietic stem cells reveals an apoptosis-independent role for p53 in self-renewal" *Cell Stem Cell*, 7:186-197.

Mohrin, M. et al. (2010) "Hematopoietic stem cell quiescence promotes error-prone DNA repair and mutagenesis" *Cell Stem Cell*, 7:174-185.

Naim, V. & Rosselli, F. (2009) "The FANC pathway and BLM collaborate during mitosis to prevent micro-nucleation and chromosome abnormalities" *Nat Cell Biol*, 11:761-768, including Methods and Supplementary Material, 6 pages.

Nakanishi, K. et al. (2005) "Human Fanconi anemia monoubiquitination pathway promotes homologous DNA repair" *Proc Natl Acad Sci USA*, 102:1110-1115.

Niedernhofer, L.J. (2008) "DNA repair is crucial for maintaining hematopoietic stem cell function" *DNA Repair (Amst)*, 7:523-529.

Pang, Q. & Andreassen, P.R. (2009) "Fanconi anemia proteins and endogenous stresses" Mutat Res, 668:42-53.

Pace, P. et al. (2010) "Ku70 corrupts DNA repair in the absence of the Fanconi anemia pathway" *Science*, 329:219-223.

Pang, Q. et al. (2000) "The Fanconi anemia protein FANCC binds to and facilitates the activation of STATI by gamma interferon and hematopoietic growth factors" *Mol Cell Biol*, 20:4724-4735.

Pang, Q. et al. (2001) "FANCC interacts with Hsp70 to protect hematopoietic cells from IFN-gamma/TNF-alpha-mediated cytotoxicity" *EMBO J*, 20:4478-4489.

Parmar, K. et al. (2010) "Hematopoietic stem cell defects in mice with deficiency of Fancd2 or Usp1" *Stem Cells*, 28:1186-1195.

Pefault De Latour et al., "Allogeneic hematopoietic stem cell transplantation in Fanconi anemia: the European Group for Blood and Marrow Transplantation experience," Blood, 122(26):4279-4286 (2013).

PCT International Preliminary Report on Patentability in International Patent Application No. PCT/US2016/019625, dated Aug. 29, 2017, 14 pages.

PCT International Search Report and Written Opinion in International Patent Application No. PCT/US2016/019625 dated Sep. 1, 2016, 20 pages.

PCT International Preliminary Report on Patentability in International Patent Application No. PCT/US2016/019626, dated Sep. 8, 2017, 11 pages.

PCT International Search Report and Written Opinion in International Patent Application No. PCT/US2016/019626 dated May 3, 2016, 15 pages.

Pulliam-Leath, A.C. et al. (2010) "Genetic disruption of both *Fancc* and *Fancg* in mice recapitulates the hematopoietic manifestations of Fanconi anemia" *Blood*, 116:2915-2920.

Raaijmakers, M.H. et al. (2010) "Bone progenitor dysfunction induces myelodysplasia and secondary leukaemia" *Nature*, 464:852-857, including Full Methods, 2 pages.

Rose et al., "Oxandrolone for the Treatment of Bone Marrow Failure in Fanconi Anemia," Pedatr Blood Cancer, 61:11-19 (2014).

Ruzankina, Y. et al. (2007) "Deletion of the developmentally essential gene *ATR* in adult mice leads to age-related phenotypes and stem cell loss" *Cell Stem Cell*, 1:113-126.

Seita, J. et al. (2010) "Differential DNA damage response in stem and progenitor cells" *Cell Stem Cell*, 7:145-147.

Shah, A H, et al., "Suppression of tumor metastasis by blockade of transforming growth factor beta signaling in bone marrow cells through a retroviral-mediated gene therapy in mice", Cancer Research, American Associateion for Cancer Research, US, Dec. 15, 2002, vol. 62, No. 24, pp. 7136-7138.

Shimamura, A. & Alter, B.P. (2010) "Pathophysiology and management of inherited bone marrow failure syndromes" *Blood Reviews*, 24:101-122.

Svahn Johanna, et al., "p38 mitogen-activated protein kinase inhibition enhances in vitro erythropoiesis of Fanconi anemia, complementation group A-deficient bone marrow cells", Experimental Hematology, Dec. 19, 2014, vol. 43, No. 4, pp. 295-299.

(56)          References Cited

OTHER PUBLICATIONS

Tulpule, A. et al. (2010) "Knockdown of Fanconi anemia genes in human embryonic stem cells reveals early developmental defects in the hematopoietic lineage" *Blood*, 115:3453-3462.

Vaidya et al., "TGF-ß signaling and its role in the regulation of hematopoietic stem cells," Systems and synthetic biology, Jun. 2015, 9(1):1-0.

Vinciguerra, P. et al. (2010) "Cytokinesis failure occurs in Fanconi anemia pathway-deficient murine and human bone marrow hematopoietic cells" *J Clin Invest*, 120:3834-3842.

Wakefield et al., "TGF-ß signaling: positive and negative effects of tumorigenesis,"Current opinion in genetics & development, Feb. 2002, 12(1):22-9.

Walter et al., "Exit from dormancy provokes DNA-damage-induced attrition in haematopoietic stem cells," Nature, Apr. 2015, 520(7548):549-52.

Wu, J.H. & Jones, N.J. (2012) "Assessment of DNA interstrand crosslinks using the modified alkaline comet assay" *Methods Mol Biol*, 817:165-181.

Younghoon Kee et al., "Molecular pathogenesis and clinical management of Faconi anemia", Jounal of Clinical Investigation, Nov. 1, 2002, vol. 122, No. 11, pp. 3799-3806.

Zeidler et al., "Hematopoietic growth factors for the treatment of inherited cytopenias," InSeminars in hematology, Jul. 2007, 44(3):133-37.

Zhang Haojian, et al., "TGF-beta Pathway Inhibition Rescues the Function of Hematopoietic Stem and Progenitor Cells Derived from Patients with Faconi Anemia", Blood, & 57th Annual Meeting of the American—Society-of-Hematology, Dec. 2015, vol. 126, No. 23.

Zhang Haojian, et al.,"Bone Marrow Failure in Fanconi Anemia from Hyperactive TGF-beta Signaling", BLOOD, & 56th Annual Meeting of American-Society-Of-Hematology, Dec. 2014, vol. 124, No. 21.

Zhang, Q-S et al. (2010) "*Fancd2–/–*mice have hematopoietic defects that can be partially corrected by resveratrol"*Blood*, 116:5140-5148.

Zhou, L. et al. (2008) "Inhibition of the TGF-beta receptor I kinase promotes hematopoiesis in MDS" *Blood*, 112:3434-3443.

Zhou, L. et al. (2010) "Reduced SMAD7 leads to overactivation of TGF-beta signaling in MDS that can be reversed by a specific inhibitor of TGF-beta receptor I kinase" *Cancer Res*, 71:955-963.

Zingariello, M. et al. (2013) "Characterization of the TGF-beta1 signaling abnormalities in the Gata1$^{low}$ mouse model of myelofibrosis" *Blood*, 121:3345-3363.

Brown, Christopher B., et al. "Antibodies to the type II TGBß receptor block cell activation and migration during atrioventricular cushion transformation in the heart." Developmental biology 174.2 (1996): 248-257.

Rose et al. Pediatr. Blood Cancer, Jan. 2014, vol 61(1):11-19 (Year: 2014).

Aagaard et al. RNAi therapeutics: Principles, prospects and challenges. Advanced Drug Delivery Reviews 59 (2007) 75-86 (Year: 2007).

Warzocha et al. Antisense Strategy: Biological Utility and Prospects in the Treatment of Hematological Malignancies. Leukemia and Lymphoma, vol. 24. pp. 267-281 (Year: 1997).

Vajdos et al. Comprehensive Functional Maps of the Antigen binding Site of an Anti-ErbB2 Antibody Obtained with Shotgun Scanning Mutagenesis. J Mol Biol. Jul. 5, 2002;320(2):415-28 (Year: 2002).

Brown et al. Tolerance to Single, but Not Multiple, Amino Acid Replacements in Antibody V, CDR2. J Immunol. May 1996; 156(9):3285-91 (Year: 1996).

Guido et al. Virtual Screening and Its Integration with Modern Drug Design Technologies. Curr Med Chem. 2008; 15(1):37-46) (Year: 2008).

Clark et al. Discovery and Development of Janus Kinase (JAK) Inhibitors for Inflammatory Diseases. J. Med. Chem., 2014, 57 (12), pp. 5023-5038 (Year: 2014).

Adamson, et al., "A Genome-Wide Homologous Recombination Screen Identifies the RNA-Binding Protein RBMX as a Component of the DNA-Damage Response," Nature Cell Biology, 2012, vol. 14, pp. 318-328.

Alan D'Andrea for U.S. Appl. No. 16/688,412, filed Nov. 19, 2019.

Ganapathy V., et al., "Targeting the Transforming Growth Factor-Beta Pathway Inhibits Human Basal-Like Breast Cancer Metastasis," Molecular Cancer, Biomed Central, London, GB, May 26, 2010, vol. 9, No. 1, p. 122, 16 Pages.

Gribskov M., et al., "Sequence Analysis Primer," M Stockton Press, 1991.

Griffin A.M., et al., "Computer Analysis of Sequence Data," Humana Press, 1994.

Lacouture M.E., et al., "Cutaneous Keratoacanthomas/Squamous Cell Carcinomas Associated with Neutralization of Transforming Growth Factor Beta by the Monoclonal Antibody Fresolimumab (GC1008)," Cancer Immunology and Immunotherapy, Jan. 13, 2015, vol. 64, No. 4, pp. 437-446.

Lesk A.M., Computational Molecular Biology, Oxford University Press, 1988.

Luo J., et al., "A Genome-wide RNAi Screen Identifies Multiple Synthetic Lethal Interactions with the Ras Oncogene", Cell, 2009, vol. 137, pp. 835-848.

Luo J., et al., "Principles of Cancer Therapy: Oncogene and Non-oncogene Addiction", Cell, 2009, vol. 136, pp. 823-837.

Morris J.C., et al., "Phase I Study of GC1008 (Fresolimumab): A Human Anti-Transforming Growth Factor-Beta (TGFBeta) Monoclonal Antibody in Patients with Advanced Malignant Melanoma or Renal Cell Carcinoma", PLOS One, Mar. 11, 2014, vol. 9, Issue. 3, p. e90353, 11 Pages.

Ramsden C.A(ED)., "Quantitative Drug Design," Choplin Pergamon Press, Chapter 17.2, 1992.

Sigmaaldrich : "Monoclonal Anti-CD314-APC Antibody Produced in Mouse Clone 1D11, Purified Immunoglobulin, Buffered Aqueous Solution," Jan. 1, 2016, 2 Pages, Retrieved from URL: www. sigmaaldrich.com/catalog/product/sigma/sab4700720lang_de ion-De.

Smith D. W., Biocomputing: Informatics and Genome Projects, Academic Press, 1993.

Soderberg S.S., et al., "Complex and Context Dependent Regulation of Hematopoiesis by TGF-[beta] Superfamily Signaling", Annals of the New York Academy of Sciences, Sep. 1, 2009, vol. 1176, No. 1, pp. 55-69, 14 Pages.

Von Heinje G., Sequence Analysis in Molecular Biology, Academic Press, 1987.

* cited by examiner

Figure 2
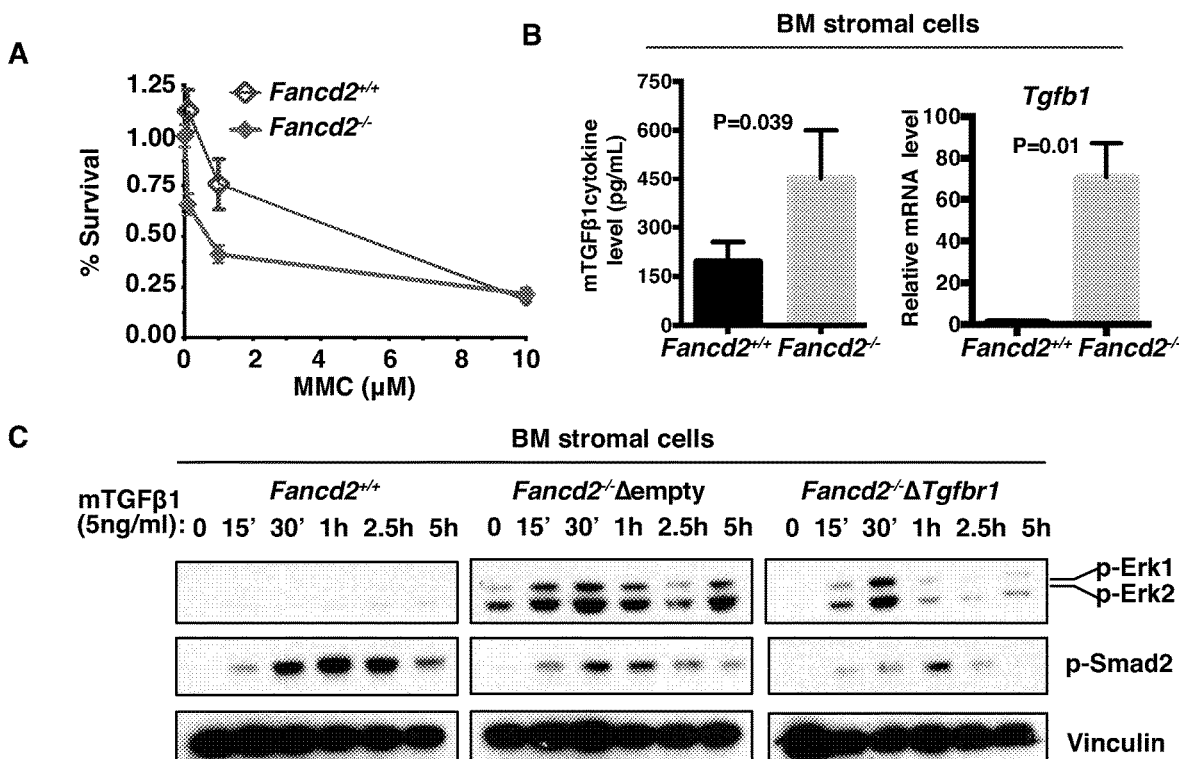
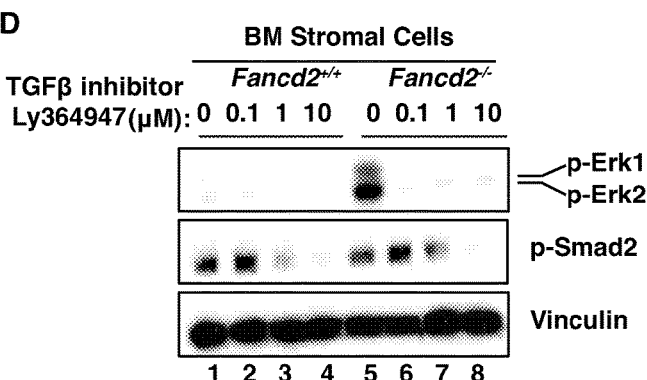

FIGURE 5 a

Healthy control          FA patients

SMAD4
SMAD1
BMP2
TGFBRAP1
SMAD7
BMPR2
SMAD9
BMP6
STAT2
TGFBR2
STAT6
BMP4
SMAD9
BMP15
BMP7
BMP8A
BMP2K
BMP1
TGFB3
STAT4 b

Patient #1 (FA-A)
(EGF017)

Number of CFU-GM

60 —
40 —
20 —
0 — shControl     shSMAD3     shTP53 c

Patient #2 (FA-A)
(EGF266)

12 —
8 —
4 —
0 — shControl     shSMAD3     shTP53 d

Patient #3 (FA-D2)
(EGF268)

30 —
20 —
10 —
0 — shControl     shSMAD3     shTP53 e

Patient #4 (FA-A)
(EGF157)

30 —
20 —
10 —
0 — shControl     shSMAD3     shTP53 f shFANCD2-Puro          shSMAD3-GFP
lentivirus                    lentivirus

CD34+ cells from     Puromycin     Sorting          Clonogenic assay
human cord blood g

*FANCD2*

Relative mRNA level 1.5 —
1.0 —
0.5 —
0.0 — p<0.0001 shControl     shFANCD2

*SMAD3*

Relative mRNA level 1.5 —
1.0 —
0.5 —
0.0 — p=0.0002 shControl     shSMAD3 h

Colony number

50 —
40 —
30 —
20 —
10 —
0 — shControl     shFANCD2     shFANCD2+SMAD3 i

CFU (% of Control)

100 —

10 —

Untreated          MMC

○ shControl
⊞ shFANCD2
△ shFANCD2/SMAD3 p=0.011

Figure 10
A
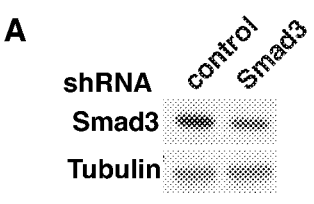
B
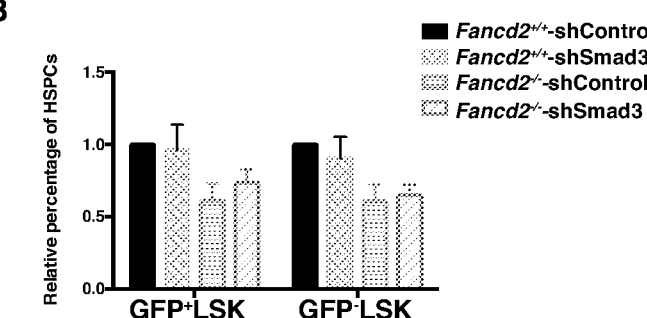

Figure 11
A
TGFβ Pathway (FA patients vs. Healthy control)
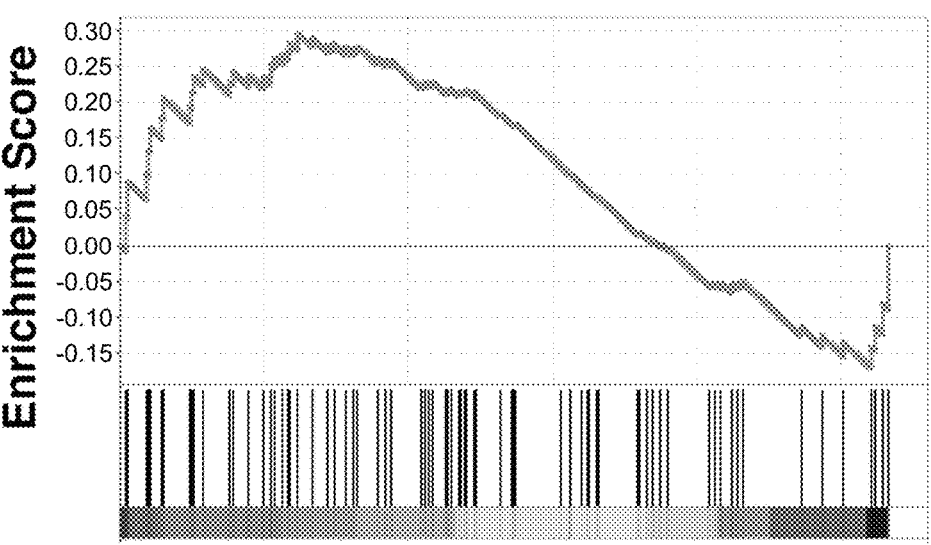
B
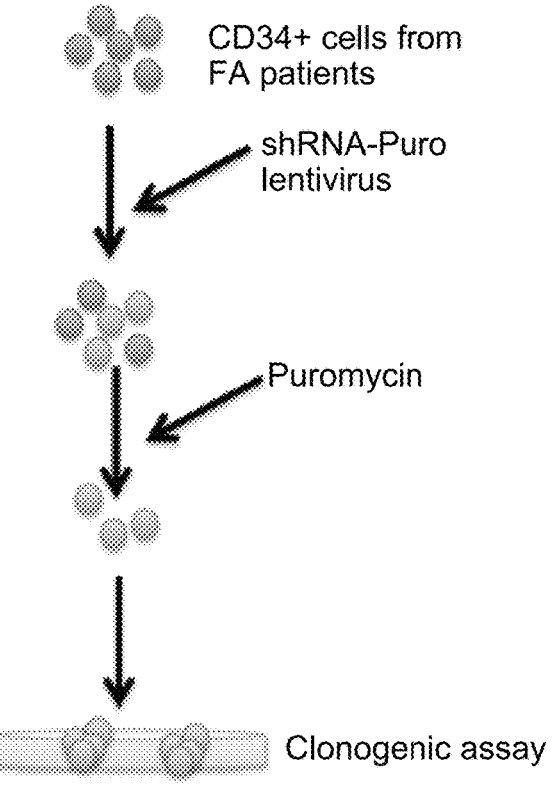

Figure 12
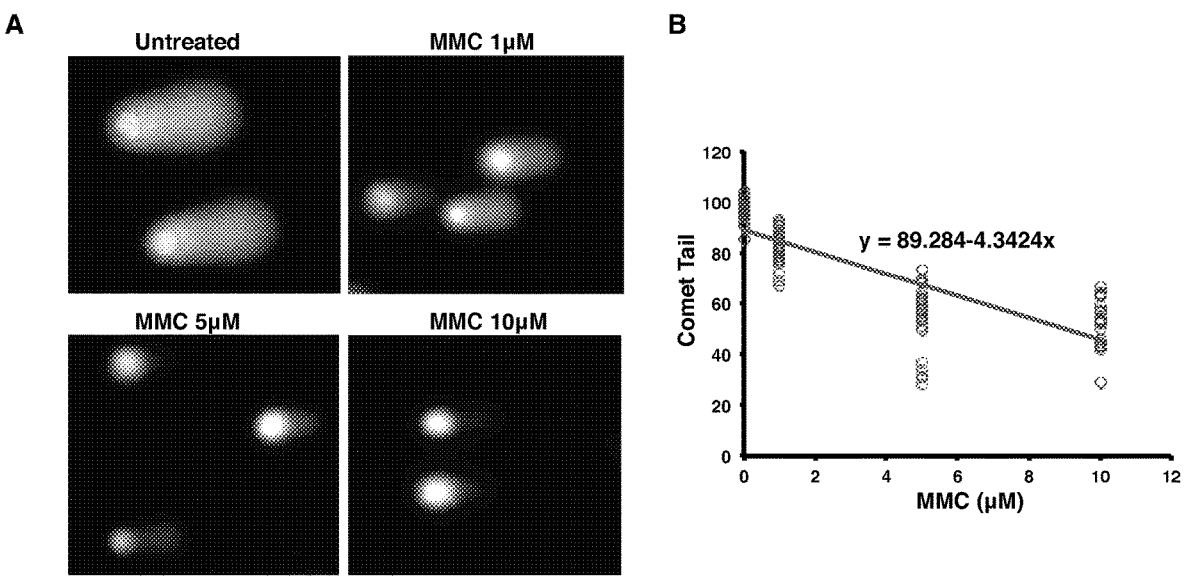
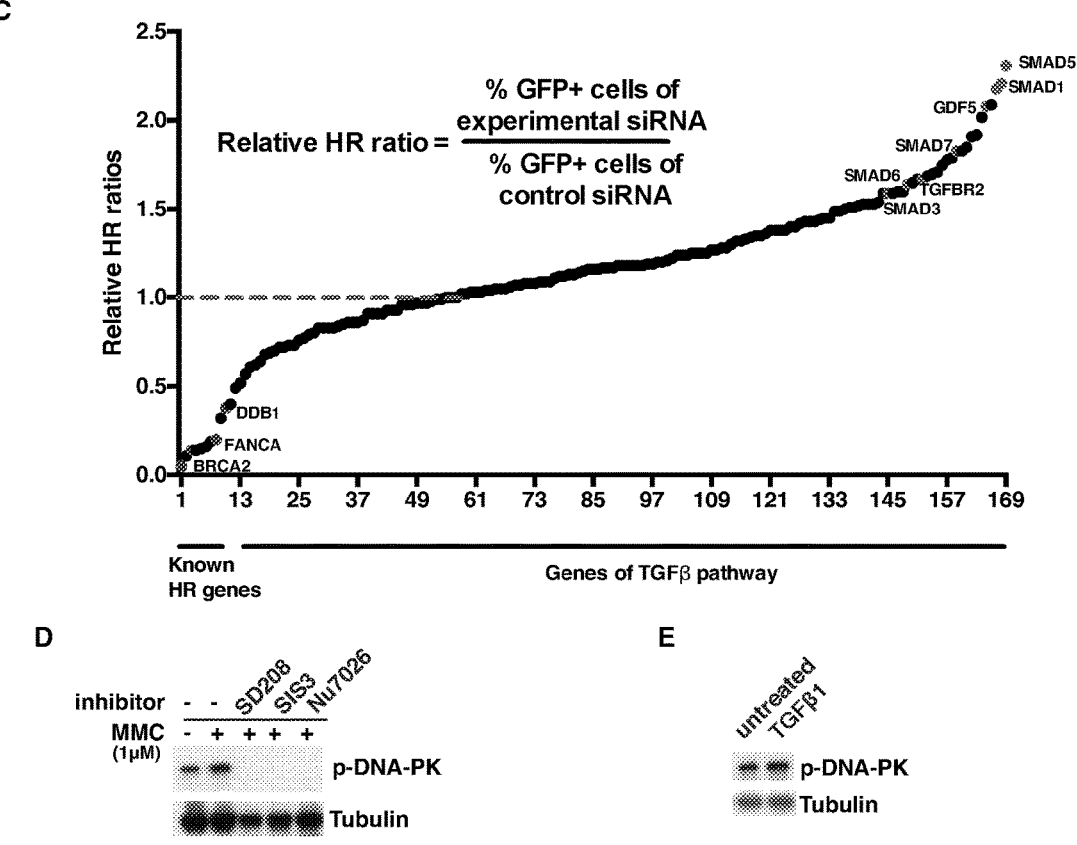

Figure 13
A
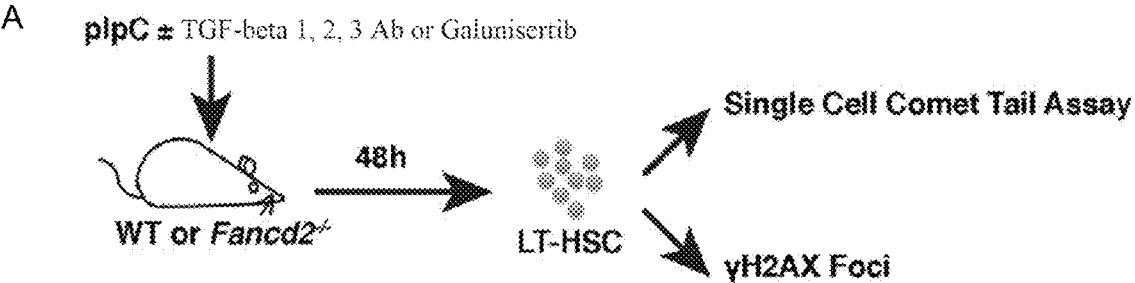
B
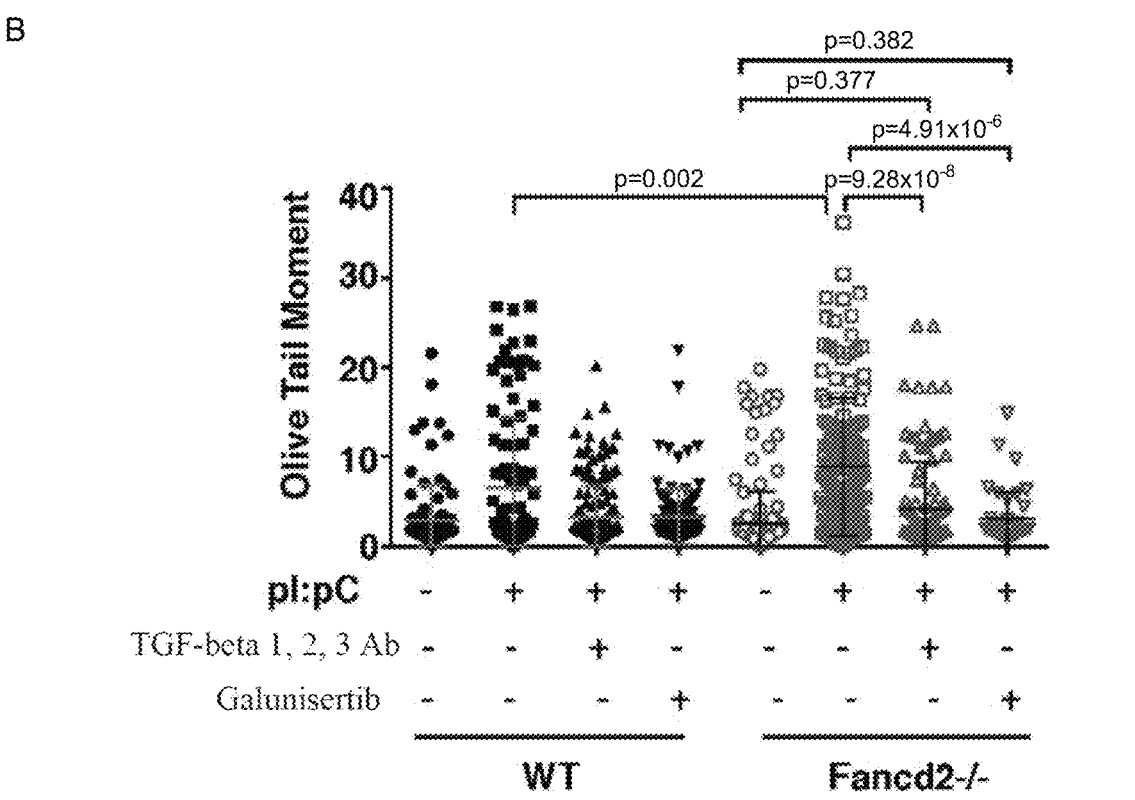
C
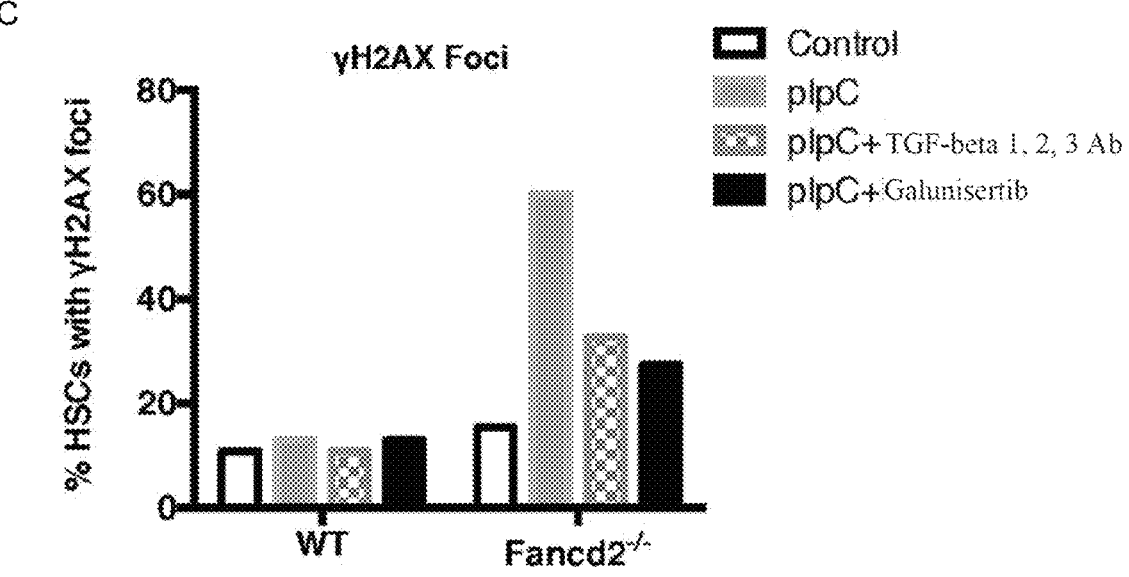

Figure 14
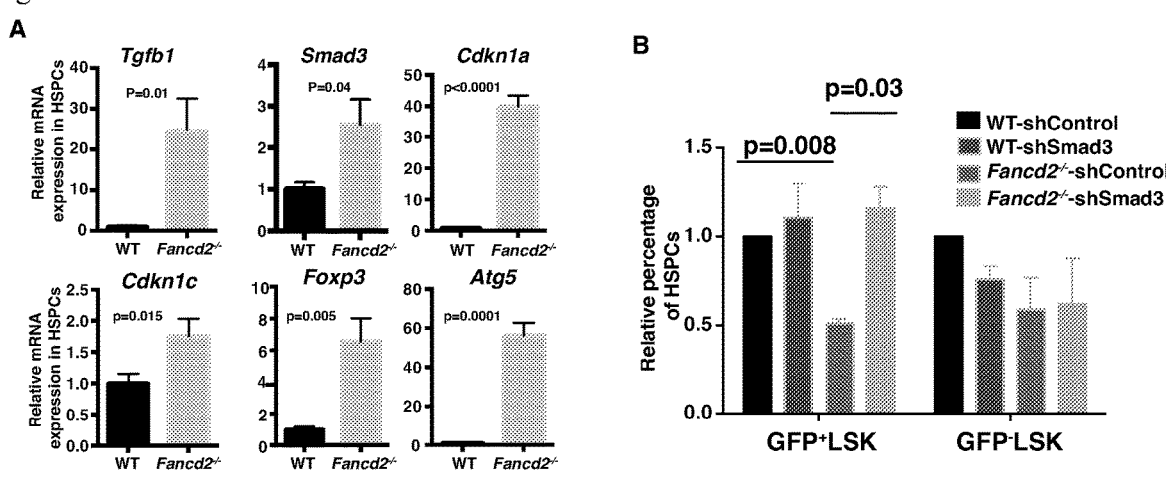
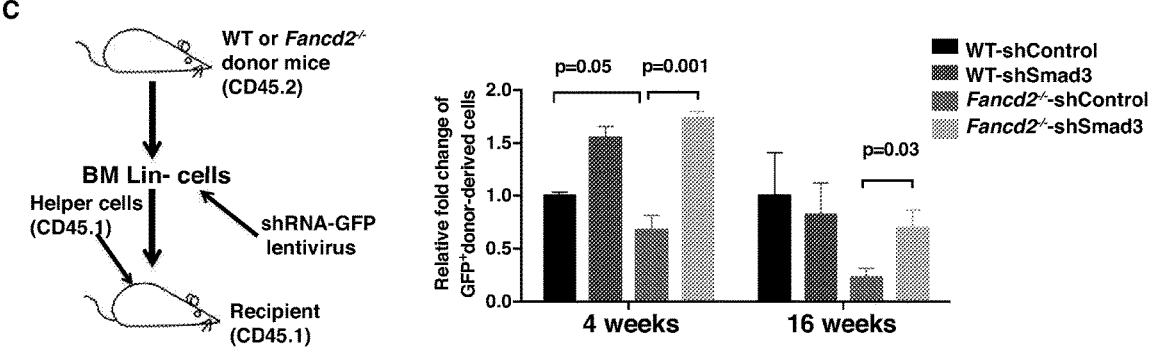
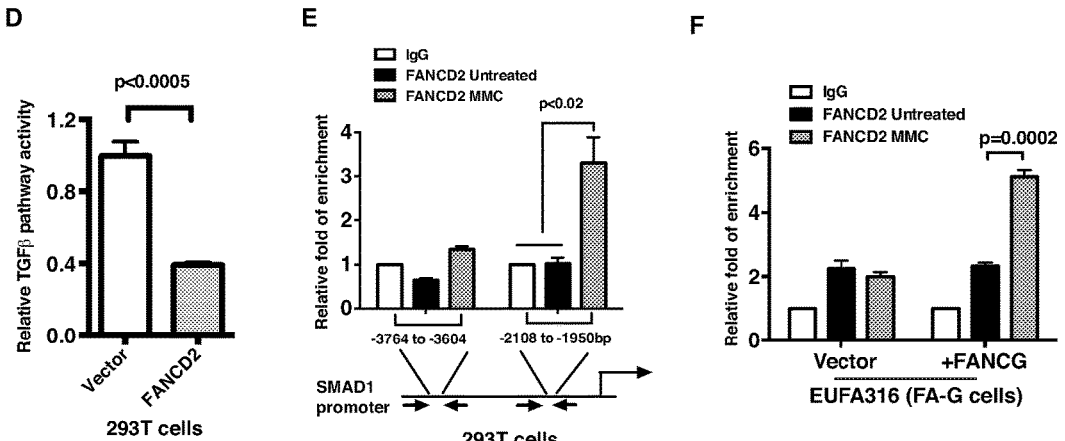

Figure 17
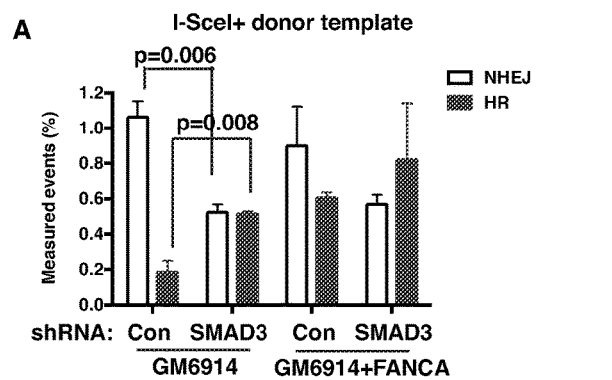
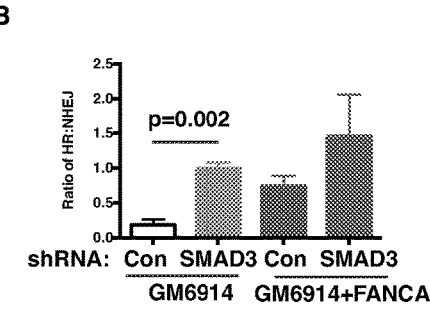
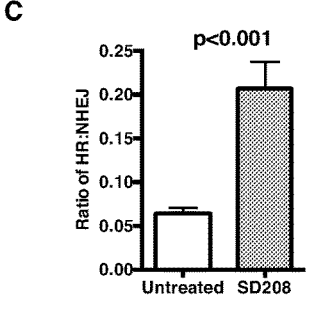
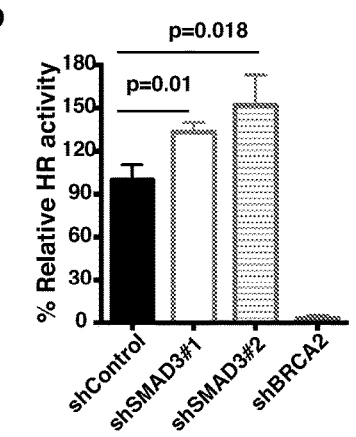
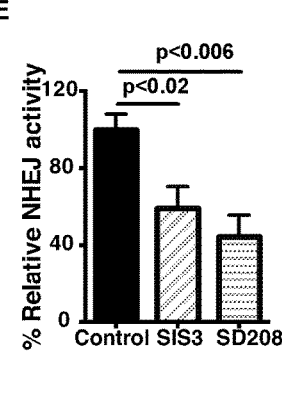
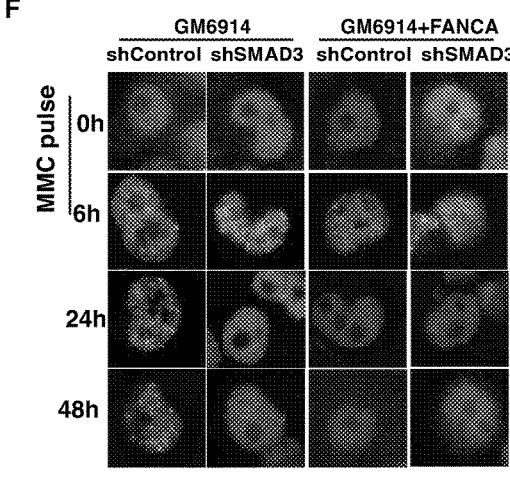
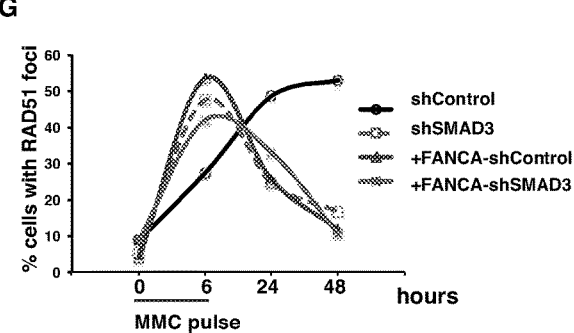

Figure 18
A
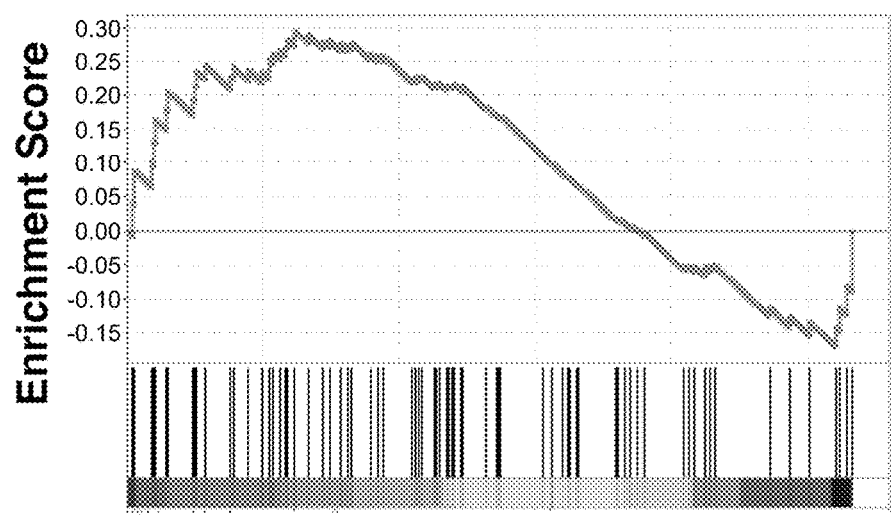
B
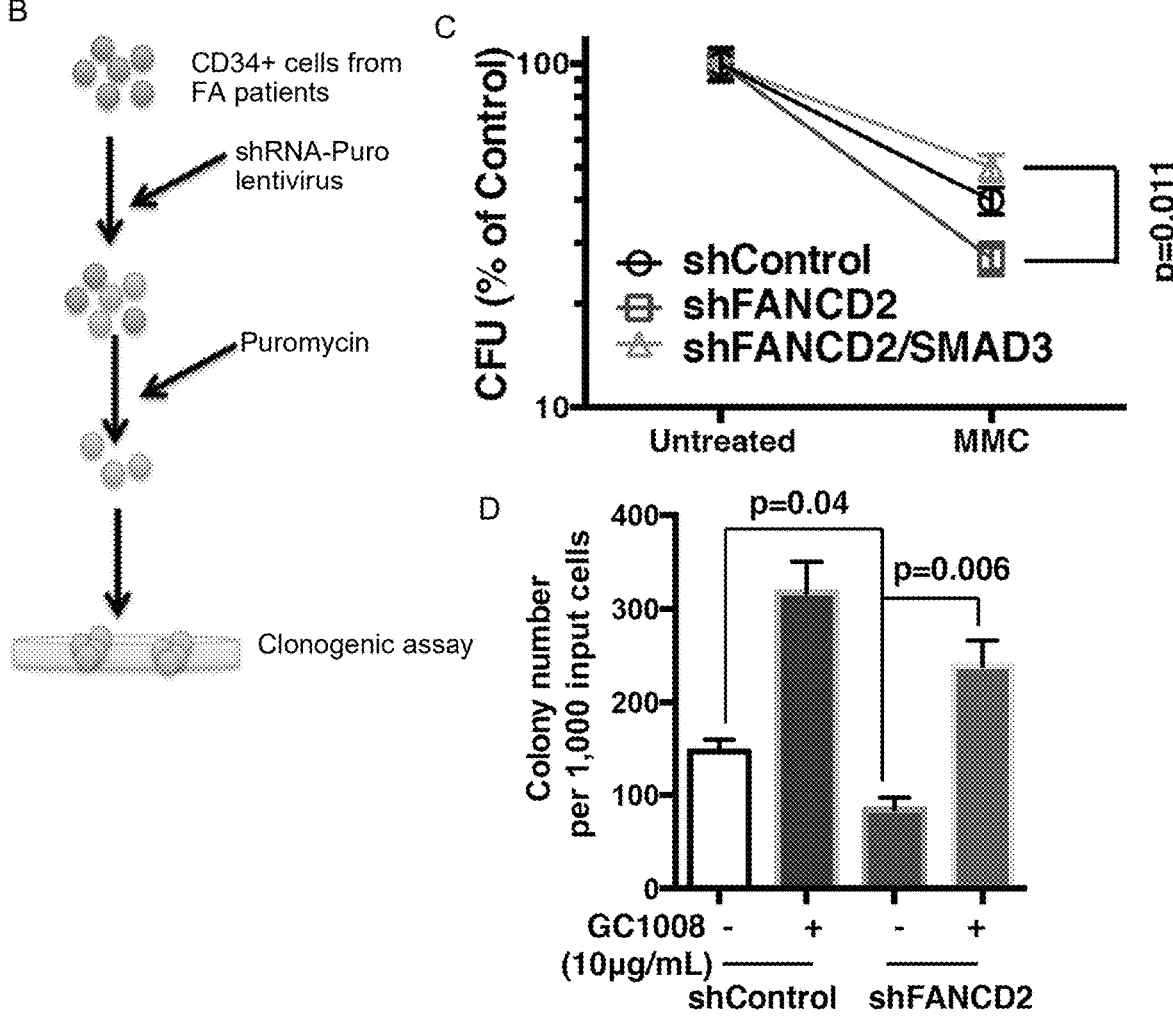

Figure 18 cont.
E
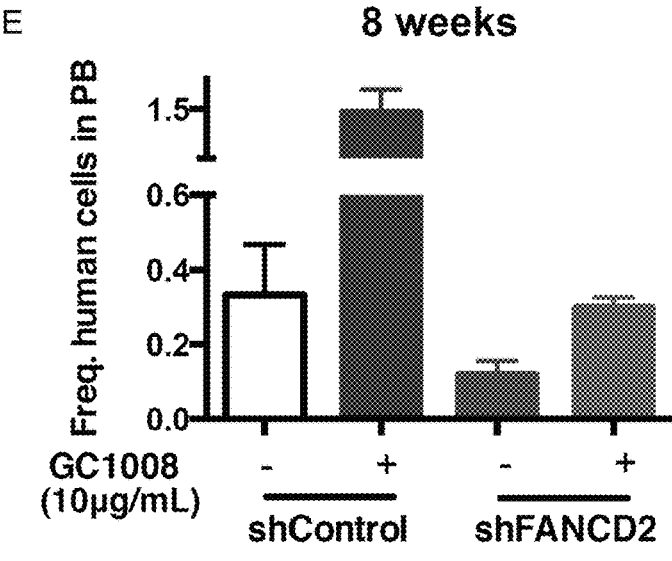
8 weeks
F
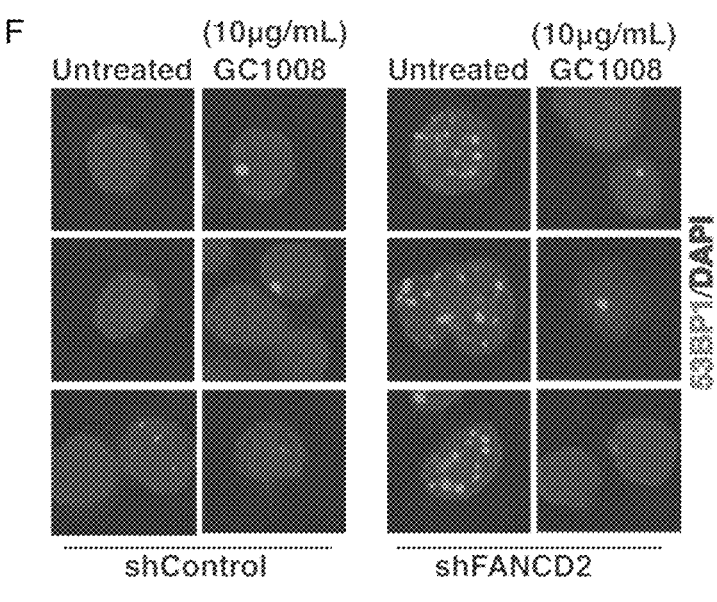
G
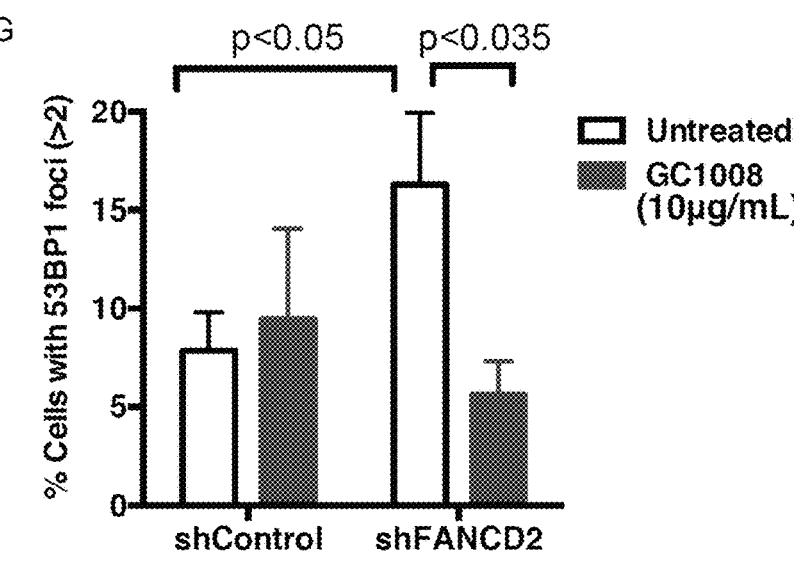

COMPOSITIONS AND METHODS OF TREATING FANCONI ANEMIA

RELATED APPLICATIONS

This application is a divisional application of U.S. application Ser. No. 15/553,905, filed Aug. 25, 2017, which is the § 371 U.S. National Stage of International Application No. PCT/US2016/019625, filed Feb. 25, 2016, which claims the benefit of U.S. Provisional Application No. 62/120,593, filed Feb. 25, 2015, the disclosures of which are incorporated by reference herein in their entireties.

FIELD OF THE INVENTION

The present invention relates generally to treating, preventing, or delaying the onset of bone marrow failure associated Fanconi Anemia.

INCORPORATION-BY-REFERENCE OF SEQUENCE LISTING

This application contains a Sequence Listing electronically submitted to the United States Patent and Trademark Office via Patent Center as an XML file entitled "DFCI-1965US02_1687440708276" having a size of 14.8 kilobytes and created on Jun. 22, 2023. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

BACKGROUND OF THE INVENTION

Fanconi Anemia (FA) is an autosomal recessive DNA repair disorder characterized by congenital abnormalities, cancer predisposition, and progressive bone marrow failure (BMF). FA is caused by biallelic mutations in one of sixteen FANC genes, the products of which cooperate in the FA/BRCA DNA repair pathway. Although the precise biochemical functions of the FA/BRCA pathway remain unclear, the pathway promotes homologous recombination (HR) repair. The FA/BRCA pathway also regulates cytokinesis, and pathway disruption results in increased binucleate bone marrow cells and apoptosis. FA cells are also uniquely hypersensitive to oxidative stress and apoptotic cytokines, such as IFNγ and TNFα.

BMF of FA patients is attributable to impaired stem cell pool. FA patients develop progressive bone marrow failure during childhood, and frequently require an allogeneic or unrelated donor bone marrow transplant. All blood lineages are deficient in FA patients suggests that the FA pathway regulates the function of hematopoietic stem and progenitor cells (HSPCs). CD34$^+$ cells of FA patients, which are a human stem cell/progenitor cell enriched population, were not only lower in the number, but also exhibited compromised clonogenicity. Similarly, mice with Fanc mutations also displayed reduced numbers of hematopoietic stem cells (HSCs) with impaired reconstitution ability. In addition, the FA pathway also controls hematopoietic development. Knockdown of FANCA and FANCD2 in human embryonic stem cells impaired embryonic hematopoiesis which could be rescued by FA gene complementation. Therefore, these studies link FA pathway with stem cell function.

The mechanism of bone marrow failure in FA remains elusive. A need exist for a better understanding of the mechanism of BMF in FA as well as therapies to treat BMF other than bone marrow transplant.

SUMMARY OF THE INVENTION

The invention provides methods of treating, preventing or delaying the onset of bone marrow failure in a patient having Fanconi Anemia (FA) by administering to the patient a compound that inhibits the expression or activity of TGFβ.

Also include in the invention is a method of administering to a patient that has been prepared to receive a bone marrow transplant a compound that inhibits the expression or activity of TGFβ.

Further included in the invention are methods of expanding hematopoietic stem/progenitor cells by contacting a population of hematopoietic stem/progenitor cells with a compound that inhibits the expression or activity of TGFβ.

The compound is a nucleic acid, an antibody or a small molecule. The nucleic acid is for example an shRNA, siRNA or an sgRNA specific for TGFβ SMAD2, or SMAD3. The antibody is specific for TGFβ or TGFβR1. The he small molecule is for example, a DNA dependent protein kinase inhibitor, a SMAD3 inhibitor, a TGFβR1 inhibitor or a MEK1/2 inhibitor.

The composition is administered before the patient is prepared for a bone marrow transplant, after the patient receives a bone marrow transplant or after the patient is prepared for a bone marrow transplant but prior to the bone marrow transplant.

Alternatively the composition is administered when the patient is having medical crisis, such as an infection. The infection is viral or bacterial. Optionally the method further includes administering androgen therapy or erythropoietin.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTIONS OF THE DRAWINGS

FIG. 1. TGFβ pathway disruption enhances FA cellular growth.
  A) RIGER P value analysis to identify top candidate genes.
  B) Clonogenic survival of GM6914 (FA-A fibroblasts) and FANCA-corrected GM6914 cells after shRNA mediated knockdown of SMAD3. Cells were treated with increasing doses of MMC and plated for 10-12 days. The average of two experiments is presented; error bars represent s.e.m. Immunoblot in the right panel shows SMAD3 silencing efficiency.
  C) MMC sensitivity of EUFA316 (FA-G fibroblasts) and FANCG-corrected EUFA316 cells incubated with or without SMAD3 inhibitor SIS3.

D) MMC sensitivity of EUFA316 (FA-G fibroblasts) and FANCG-corrected EUFA316 cells incubated with or without TGFβ inhibitor SD208.

E) Acetaldehyde sensitivity of EUFA316 (FA-G fibroblasts) and FANCG-corrected EUFA316 cells incubated with or without TGFβ inhibitor SD208.

F) Acetaldehyde sensitivity of EUFA316 (FA-G fibroblasts) cells after shRNA mediated knockdown SMAD3 and TP53.

G) The expression of p53 and p21 was analyzed by immunoblot in GM6914 cells treated with TGFβ inhibitors SD208 or shRNA-mediated knockdown of SMAD3 and treated with MMC.

FIG. 2. Characterization of FA murine primary bone marrow stromal fibroblast.

A) Survival of Fancd2+/+ or Fancd2−/− stromal cells in the presence of MMC. Data are shown in triplicate. Error bars represent s.e.m.

B) Enhanced expression level of Tgfb1 in Fancd2−/− stromal cells. (Left panel) Active mouse Tgfβ1 serum levels in the culture supernatant of Fancd2+/+ or Fancd2−/− stromal cells were evaluated by ELISA. (Right panel) qRT-PCR analysis of Tgfb1 mRNA expression. Data are shown the average of three independent experiments. Error bars represent s.e.m.

C) Immunoblots of phosphorylated Erk1/2 in stromal cells treated with Tgfβ for the indicated time. Tgfβ induced higher level of p-Erk1/2 in Fancd2−/− stromal cells (Lane 7-12) compared to Fancd2+/+ stromal cells (Lane 1-6). Knockout of Tgfbr1, mediated by CRISPR-sgRNA in Fancd2−/− stromal cells, markedly reduced phosphorylation of Erk1/2 (Lane 13-18).

D) Immunoblot of phosphorylated Erk1/2 and Smad2 in Fancd2+/+ and Fancd2−/− stromal cells treated with TGFβ inhibitor for 4 h.

Figure 3:
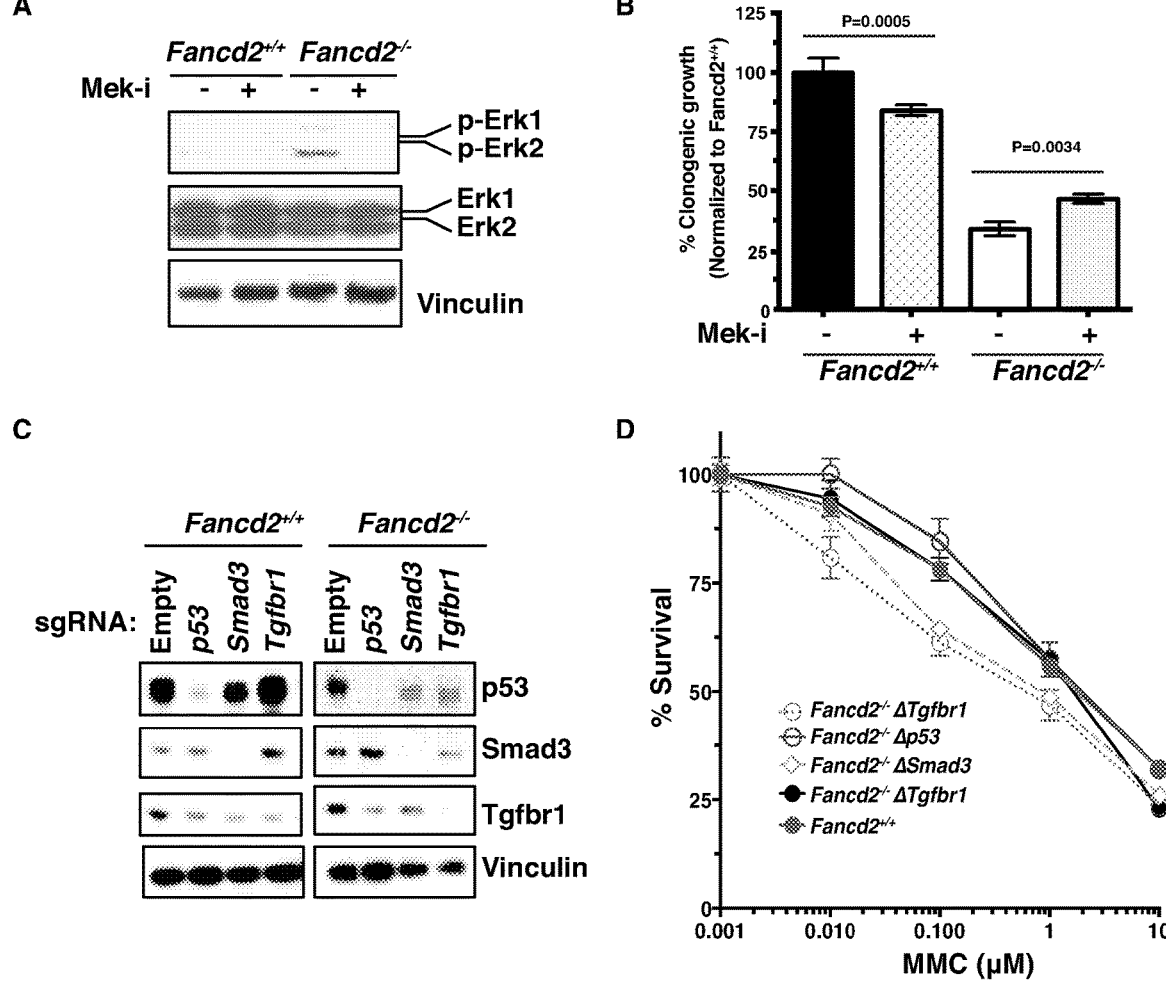

FIG. 3. Blocking non-canonical TGFβ-ERK pathway enhances FA cellular growth.

A) Mek-inhibitor treatment (Mek-i, PD0325901) reduces p-Erk1/2 expression in FA (Fancd2−/−) BM stromal cells. Fancd2+/+ stromal cells shown as a control.

B) Colony forming capacity of Fancd2−/− BM Stromal cells is improved by treatment with 1 μM Mek-i.

C) Immunoblot analysis showing deletion of Tgfbr1, Smad3 and p53 in murine Fancd2+/+ and Fancd2−/− stromal cells D) Survival of Fancd2−/− stromal cells with deletion of Tgfbr1, Smad3 or p53 in presence of MMC. Error bars represent s.e.m.

Figure 4:
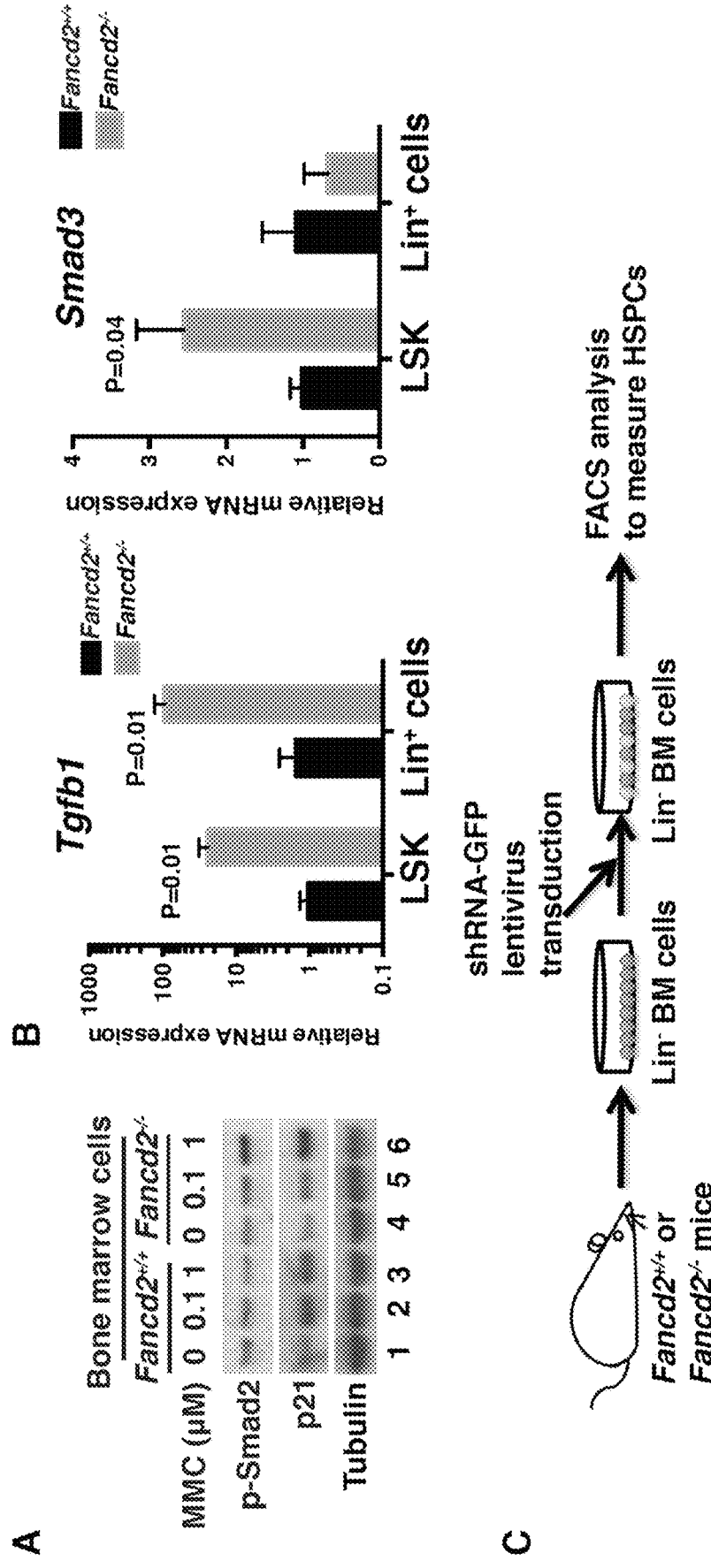
Figure 4:
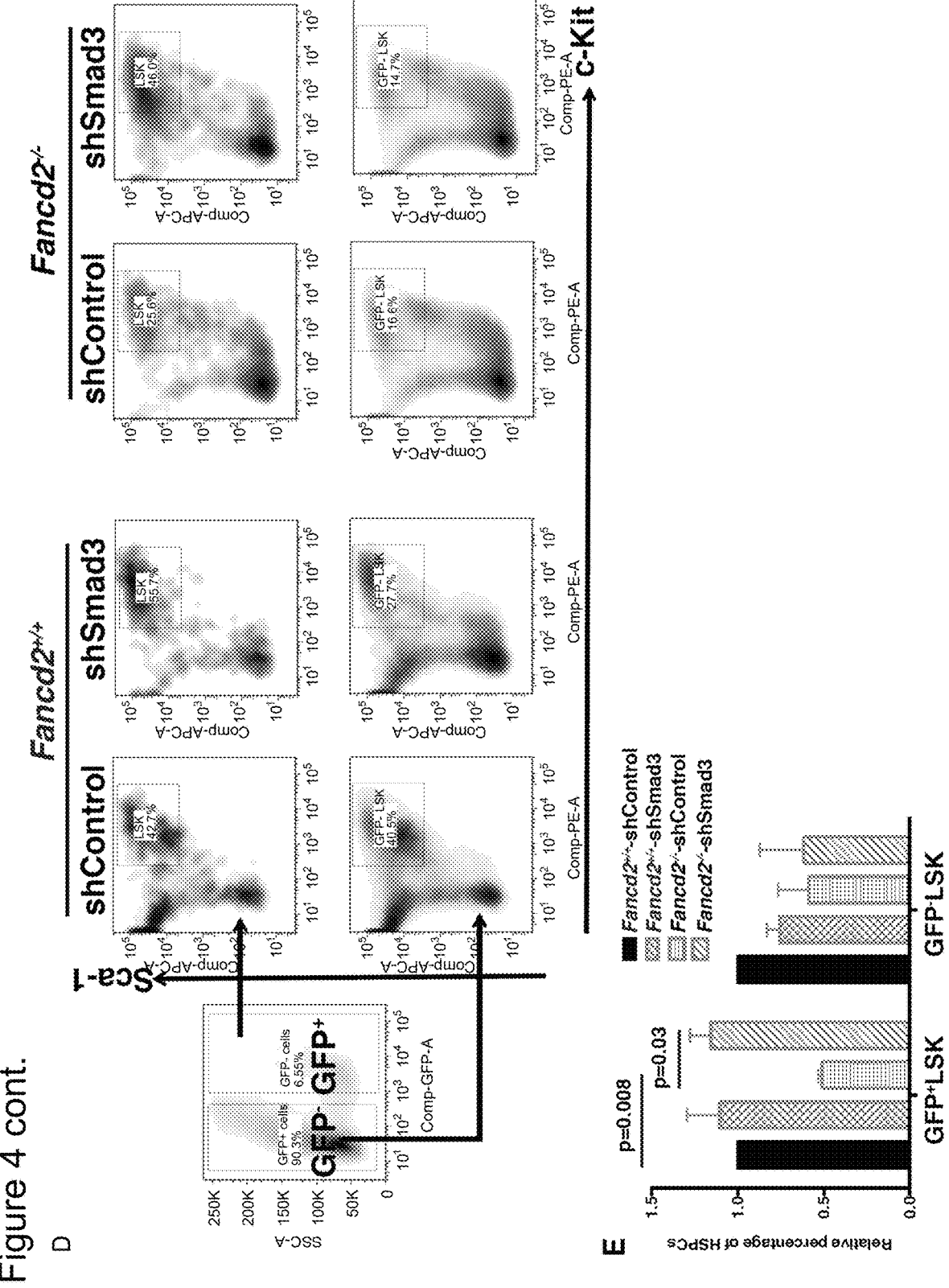

FIG. 4. Inhibition of the canonical TGFβ pathway in primary murine hematopoietic cells promotes proliferation of HSPC.

A) Immunoblot of p-Smad2 and p21 in the indicated murine Fancd2−/− whole bone marrow cells.

B) qRT-PCR analysis showing the expression level of Tgfβ1 and Smad3 in LSK and Lin+ cell populations from Fancd2+/+ and Fancd2−/− mice.

C) Schematic experimental design of lentivirus shRNA transduction of Lin− BM cells from Fancd2+/+ and Fancd2−/− mice.

D) Representative plot of LSK cells analyzed by flow cytometry after 5 days in vitro culture in stem cell culture medium.

E) Quantification of the percentage of transduced (GFP+) and non-transduced (GFP−) LSK cells after 5 days in vitro culture in stem cell culture medium. Data shown are the average of three independent experiments. Error bar represent s.e.m.

FIG. 5. TGFβ gene expression in primary bone marrow cells from FA patients.

A) Microarray analysis of selected genes in FA patients and in healthy subject controls.

B-E) In vitro assays using selected FA patient's isolated cells to determine the number of CFU-GM (Colony Forming Unit-granulocyte, monocyte) following administration of the described short hairpin constructs (i.e. shControl, shSMAD3, and shTP53).

F) Schematic depicting clonogenic assays using CD34+ human cord blood cells.

G) FANCD2 and SMAD3 gene expression assay following exposure to either shControl or either shFANCD2 or shSMAD3, respectively.

H) Graph depicting colony number following exposure to shControl, shFANCD2, or shFANCD2+SMAD3.

I) Graph depicting Colony Forming Unit (CFU) in cells that have shControl, shFANCD2, or shFANCD2+SMAD3, in either an untreated condition or treated MMC.

Figure 6:
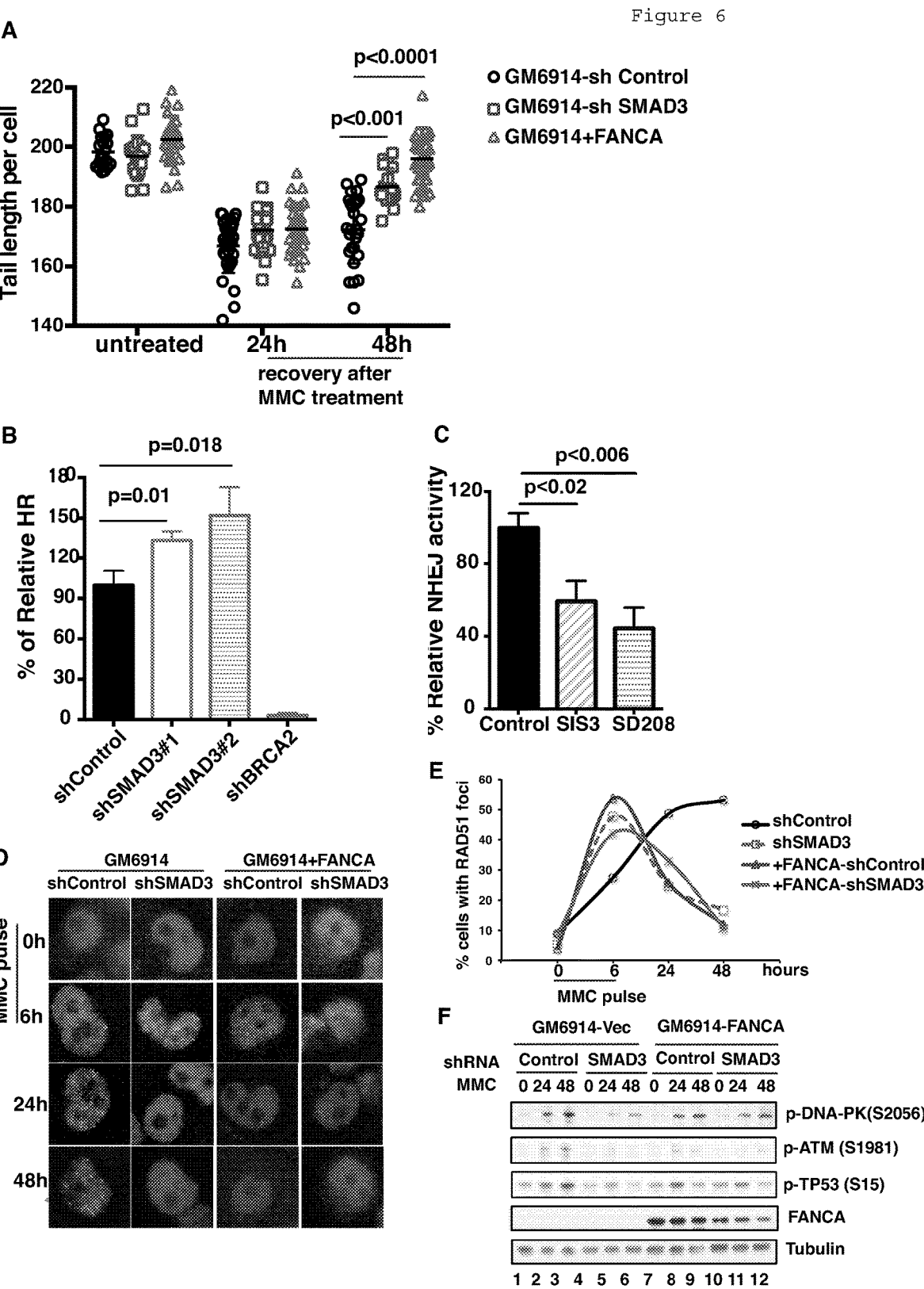

FIG. 6. Inhibition of the TGFβ pathway in FA cells modulates DNA repair activity.

A) Comet tail assay. GM6914 cells with knockdown SMAD3 by shRNA or GM6914 cells corrected with FANCA were treated with 1 μM MMC for 8 h following washing out and recovery for 24 h and 48 h. The lengths of comet tail of 30-50 cells in each group were measured. Data are representative of two independent experiments.

B) Homologous recombination assay was measured in U2OS cells with DR-GFP reporter. SMAD3 knockdown significantly increases HR efficiency. The representative of three independent experiments is presented; error bar represent s.e.m.

C) NHEJ assay showing inhibition of the TGFβ pathway by small molecule inhibitors results in decreased NHEJ activity (D and E) Representative images (D) and quantification (E) of RAD51 foci in MMC treated shControl or shSMAD3 GM6914 cells, and FANCA corrected GM6914 cells. Cells were treated with 1 μM MMC. After 6 h, cells were washed twice, and recovered for 24 h. 100 cells were counted for RAD51 foci.

F) Immunoblot of DNA damage response signaling including p-ATM, p-TP53 and p-DNA-PK and p21 in FA cells. GM6914 cells with knockdown SMAD3 and TP53 by shRNA or GM6914 cells corrected with FANCA were treated with 1 μM MMC for 8 h following washing out and recovery for 24 and 48 hours.

Figure 7:
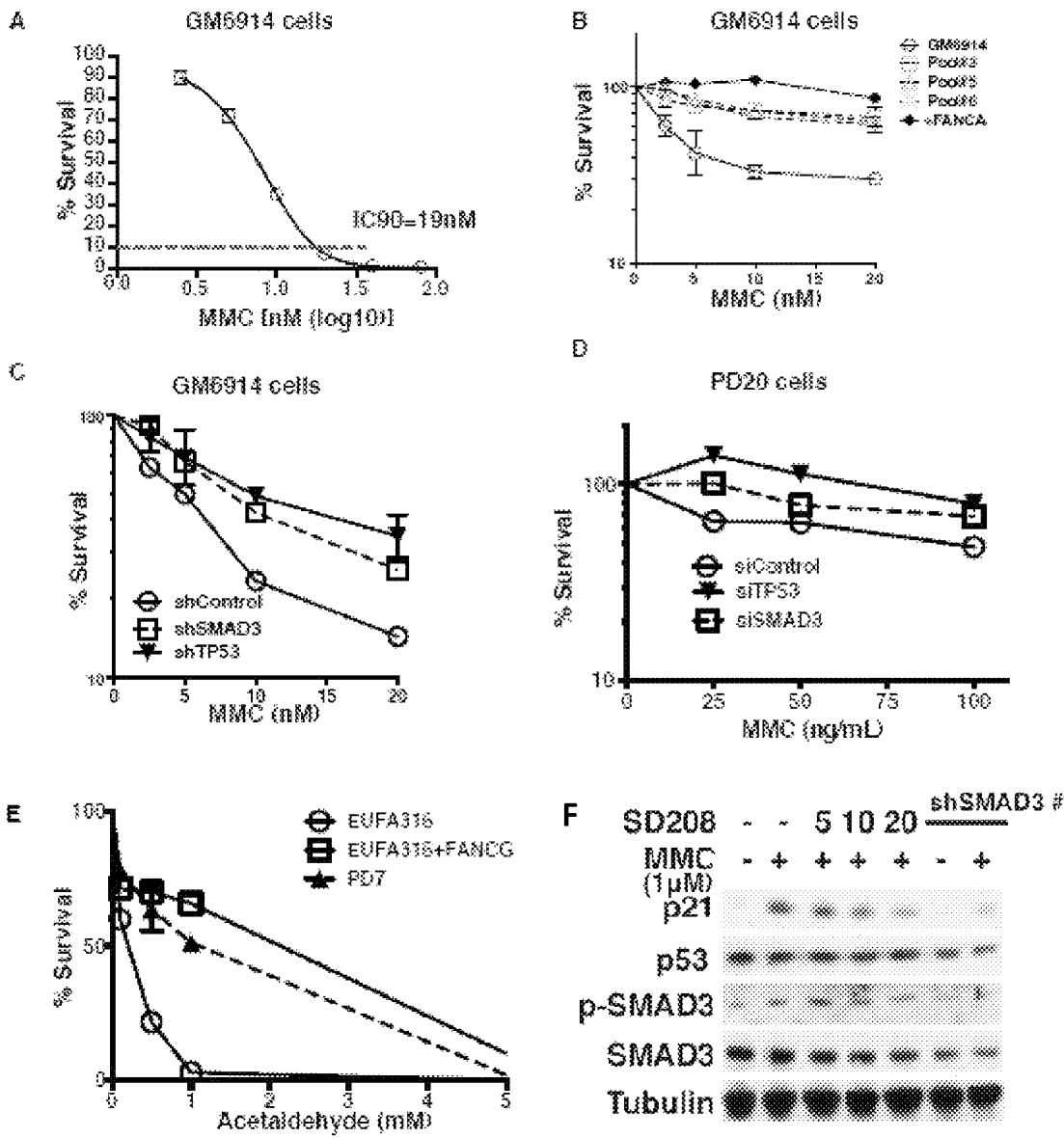

FIG. 7. Identification of IC90 concentration of MMC on GM6914 and validation of genome wide RNAi screening for MMC resistance.

A) Identification of IC90 concentration of MMC on GM6914. Cells were treated with different doses of MMC for 7 days, and cell viability was measured using CellTiterGlo reagent. The IC90 of MMC is 19 nM for GM6914.

B) Reassessment of MMC sensitivity of cells after virus infection and MMC treatment. Cells were transduced with 6 pools of shRNA retrovirus libraries, and selected with puromycin for 48 h. Cells were then treated with MMC for 7 days, and resistant cells were harvested to re-assess their MMC sensitivity by treated with MMC for 3 days. Data shown represented cells transduced by pool #3, 5 and 6.

C) FANCA deficient fibroblast cells (GM6914) were evaluated for MMC sensitivity after shRNA mediated knockdown of SMAD3 and TP53. Survival was measured after 3 days exposure to indicated concentrations of MMC. Data shown are representative of two independent experiments. Error bars represent s.e.m.

D) FANCD2 deficient fibroblast cells (PD20) were evaluated for MMC sensitivity after RNAi mediated knockdown of SMAD3 and TP53. Survival was measured after 3 days exposure to indicated concentrations of MMC. Data shown are representative of two independent experiments. Error bars represent s.e.m.

E) Deletion of SMAD3 caused a decrease in phosphorylation of DNA-PK (S2056) in FA cells after MMC treatment.

Figure 8:
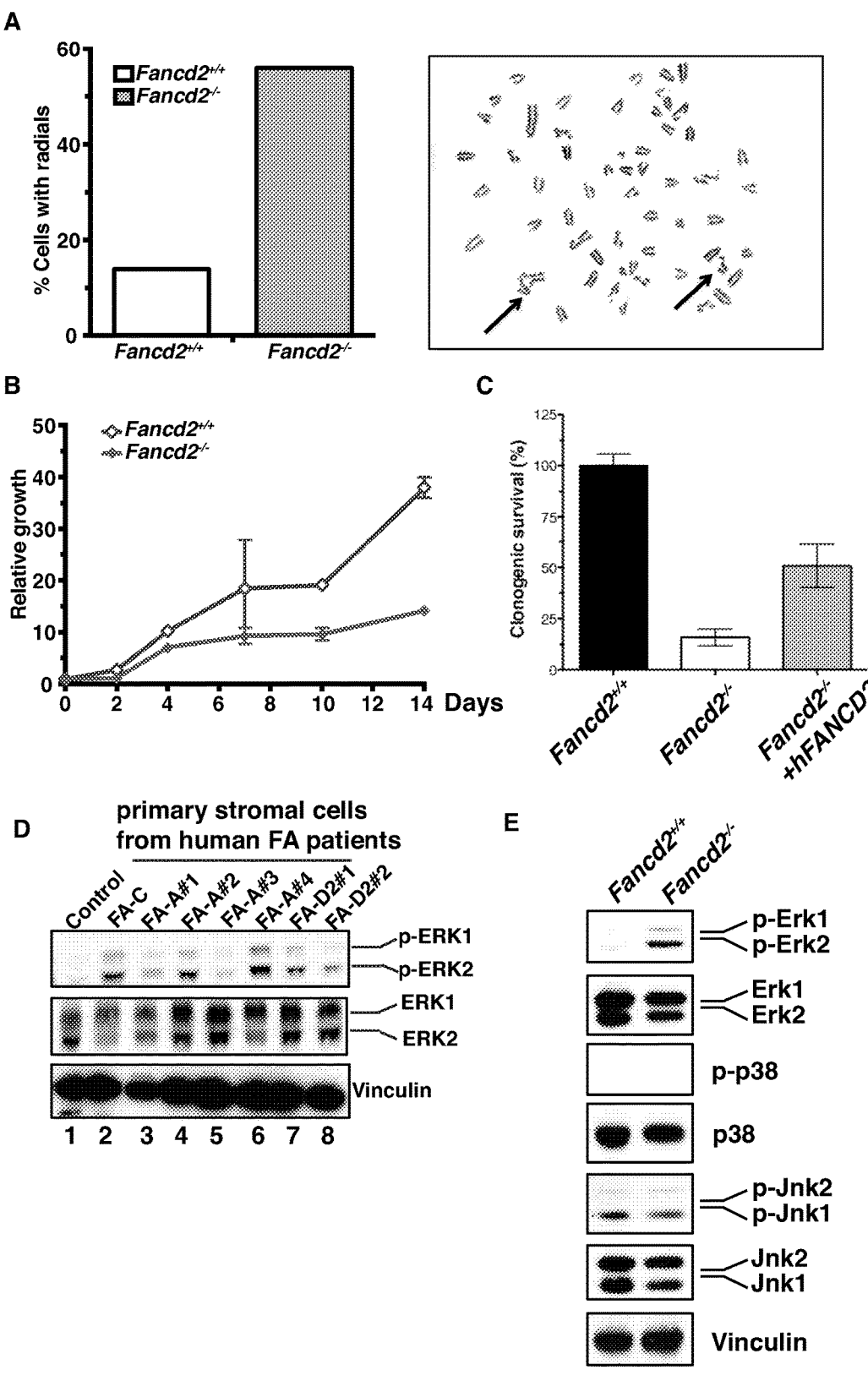

E) Acetaldehyde sensitivity assay for EUFA316 cells. Survival was measured after 3 days exposure to indicated concentrations of acetaldehyde. Data shown are representative of two independent experiments. Error bars represent s.e.m FIG. 8. Characterization of FA bone marrow stromal cells A) Fancd2−/− stromal cells display higher level of radial chromosomes after MMC treatment compared that of Fancd2+/+ stromal cells.

B) Fancd2−/− stromal cells shows defective growth ability compared to Fancd2+/+ stromal cells. Data is shown in triplicate. Error bars represent SEM.

C) Fancd2−/− BM Stromal cells showed compromised colony forming capacity compared to Fancd2+/+ stromal cells, which can be partially restored by hFANCD2.

D) Immunoblot analysis of primary BM stromal cell lines generated from FA patients compared to non-FA control stromal cells. Sub-types of each FA patient are indicated. FA-C: DF1653.B; FA-A #1: DF1238.B; FA-A #2: DF117.B; FA-A #3: FHCC-P5; FA-A #4: FHCC-73; FA-D2 #1: FHCC-42E; FA-D2 #2: FHCC196A.

E) Immunoblot showing the expression levels of p-Erk1/2, p-P38 and p-JNK in murine Fancd2+/+ and Fancd2−/− stromal cells.

Figure 9:
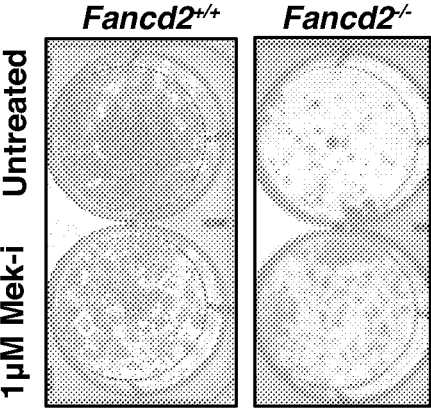

FIG. 9. Inhibition of Mek-Erk pathway partially improved the colony forming ability of Fancd2−/− stromal cells. Representative image of colonies of Fancd2+/+ and Fancd2−/− cells incubated with or without 1 μM Mek inhibitor.

FIG. 10. Inhibition of the canonical TGFβ pathway in primary murine hematopoietic cells promotes the proliferation of HSPCs A) Representative immunoblot showing knockdown of Smad3 in murine 3T3 cells.

B) Assessment of HSPCs by flow cytometry after 2 days in vitro culture. Data shown are the average of three independent experiments. Error bar represent s.e.m.

FIG. 11. Expression profiling of TGFβ pathway genes in bone marrow cells of FA patients and clonogenic assay scheme A) Gene set enrichment analysis (GSEA) displays the expression profiling of TGFβ pathway genes in bone marrow cells from FA patients and healthy control.

B) Schematic of clonogenic assay of human FA CD34+ cells

FIG. 12. Inhibition of the TGFβ pathway in FA cells promotes DNA repair activity A) Representative micrograph showing decreased comet tail length with increased MMC concentration.

B) Quantification of comet tail length displayed negative correlation with MMC concentration. The lengths of comet tail of at least 30 cells in each group were measured. Data shown in here is a representative of two independent experiments.

C) Analysis of HR siRNA screening data showing as siRNA mediated knockdown of the majority of genes of TGFβ pathway enhanced HR efficiency.

D). Representative immunoblot showing inhibition of TGFβ pathway by its inhibitors SD208 and SIS3 blocks phosphorylation of DNA-PK in U2OS cells.

E) Western immublotting analysis displayed that TGFβ treatment activates the activity of DNA-PK in U2OS cells.

FIG. 13. Inhibition of TGFβ signaling with a small molecule kinase inhibitor (Galunisertib, LY2157299) rescues physiological stress-induced bone marrow failure in mice.

A) Wild-type or Fancd2-deficient mice were exposed to the physiologic stress, pIpC. Mice were pretreated in vivo with either no Tgfβ inhibitor, the neutralizing antibody to Tgfβ 1, 2, 3, or the Tgfβ receptor kinase inhibitor, Galunisertib. Long-term HSCs (LT-HSCs) were isolated and subjected to functional tests.

B) The neutralizing antibody to Tgfβ 1, 2, 3 or the kinase inhibitor rescued the pIpC-induced DNA damage in the LT-HSCs as measured by the comet assay.

C) The neutralizing antibody to Tgfβ 1, 2, 3 or the kinase inhibitor rescued the pIpC-induced DNA damage, as measured by gamma H2AX foci.

FIG. 14. Inhibition of the TGF-β Pathway Rescues the Functional Defects of HSPCs from FA Mice.

(A) qRT-PCR analysis showing the mRNA expression levels of Tgfb1, Smad3, Cdkn1a, Cdkn1c, Foxp3 and Atg5 in LSK populations from bone marrow of WT and Fancd2−/− mice.

(B) Quantification of the percentage of transduced (GFP+) and non-transduced (GFP−) LSK cells after 5 days in vitro culture. Bone marrow Lin− cells from WT and Fancd2−/− mice were transduced with lentiviruses encoding shSmad3-GFP or shControl-GFP and cultured in triplicates for 5 days. GFP+ and GFP− LSK cells were analyzed by flow cytometry. Data shown are the average of three independent experiments. (C) Depletion of Smad3 promotes the engraftment ability of Fancd2−/− cells. Equal numbers of transduced Lin-GFP+ cells (20,000, CD45.2 cells) were transplanted into lethally irradiated recipients (CD45.1) along with 1×105 helper cells (CD45.1). Percentages of donor-derived cells (GFP+CD45.2+) in peripheral blood of recipients were analyzed at 4 and 16 weeks post bone marrow transplantation (n=5 recipient mice per group). (D) Overexpression of FANCD2 in 293T cells significantly reduced the TGF-βluciferase reporter activity. (E) FANCD2 bound to the promoter of SMAD1 in 293T cells. (F) The binding of FANCD2 to the promoter of SMAD1 was observed in corrected FA cells, but not in the parental FA cells (EUFA316), suggesting that a functional FA pathway is required for the FANCD2-mediated transcriptional decrease of the TGFβ pathway gene.

Figure 15:
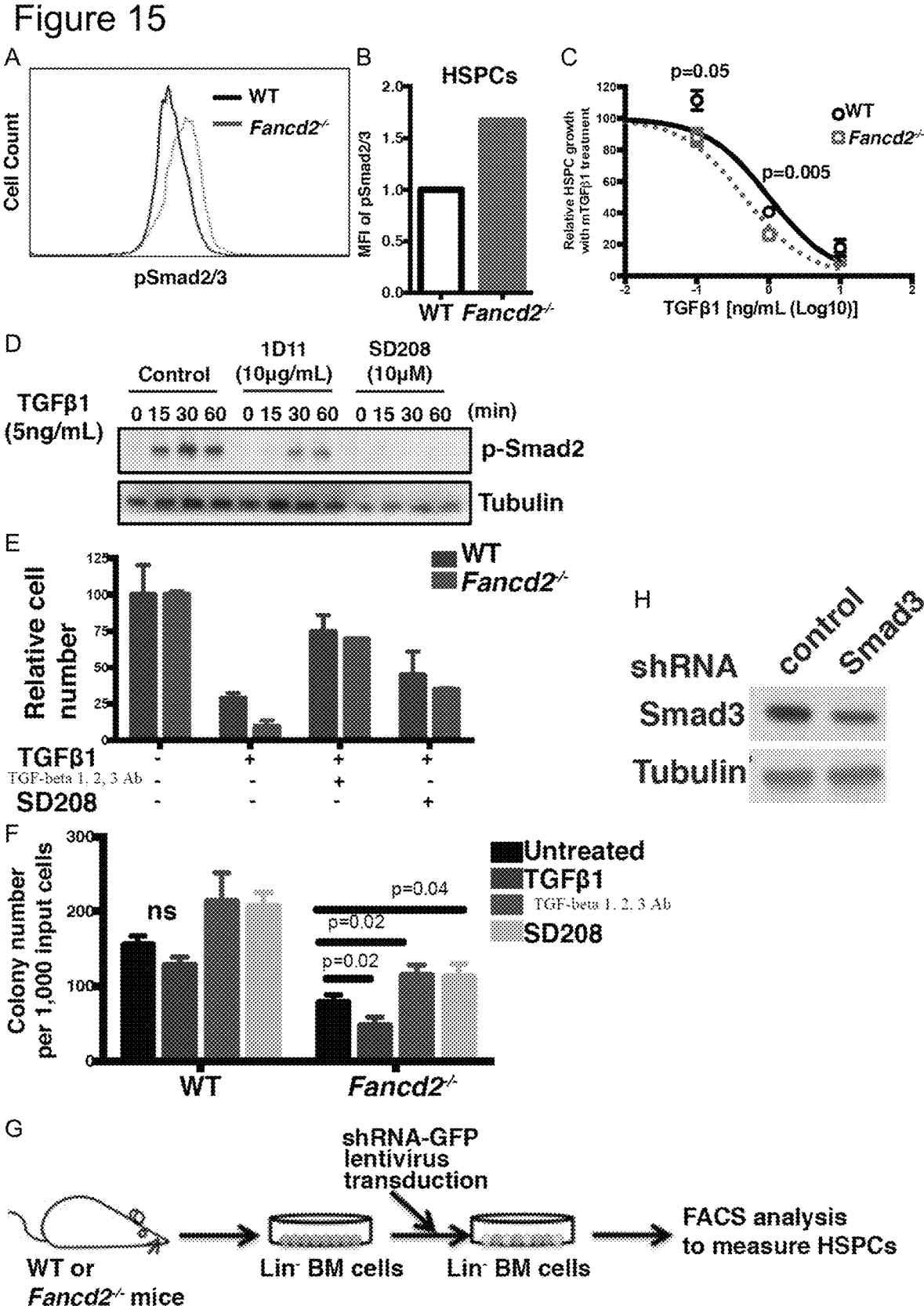
Figure 15:
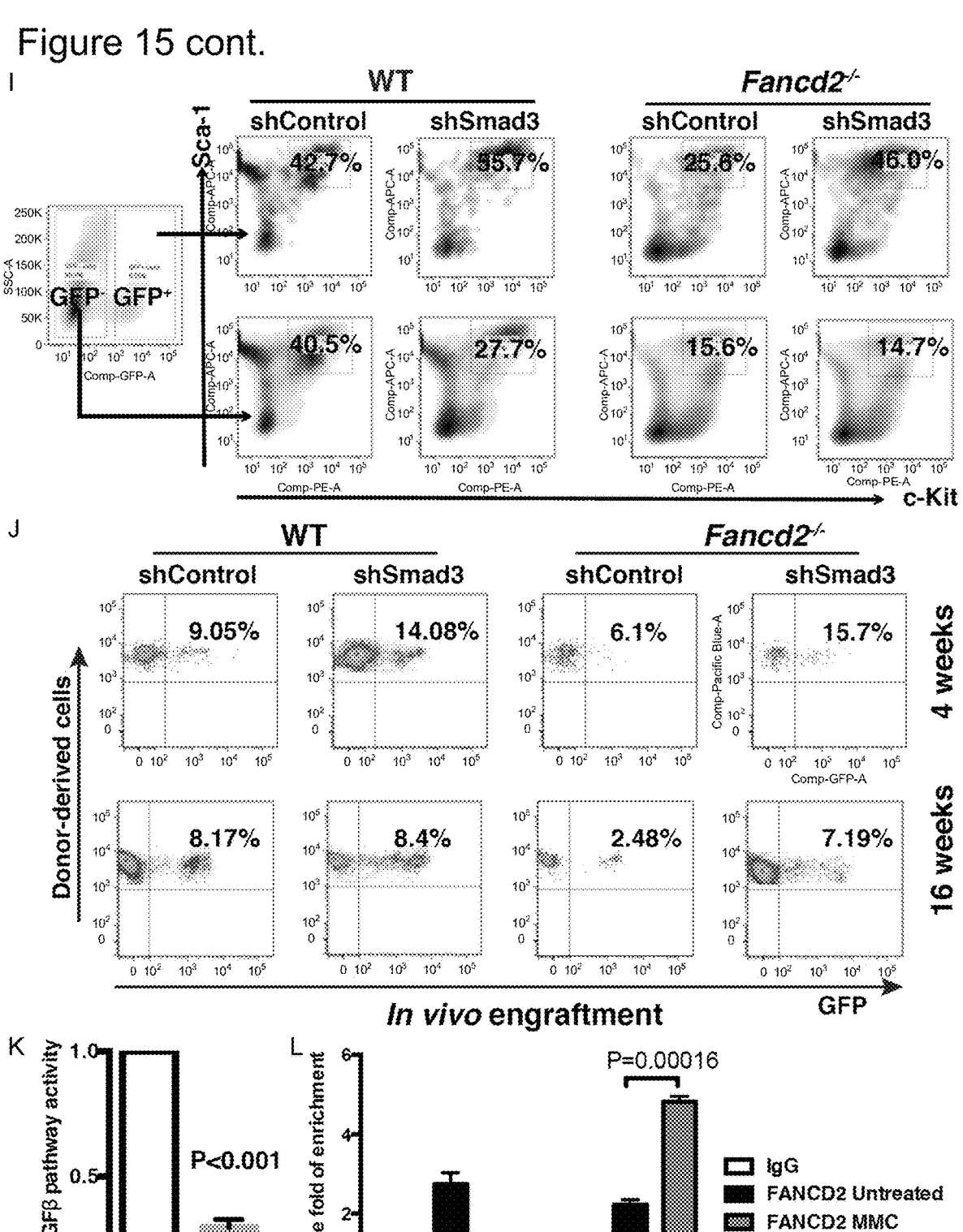

FIG. 15. HSPCs from Fancd2−/− mice display hyperactive TGFβ activity and inhibition of TGFβ signaling promotes their proliferation.

(A) Expression of phospho-Smad2/3 proteins in HSPCs from WT and Fancd2−/− mice as detected by flow cytometric analysis. (B) Quantification of mean fluorescence intensity (MFI) of phospho-Smad2/3 staining by flow cytometric analysis shown in (A) in HSPCs from WT and Fancd2−/− mice. (C) Fancd2−/− HSPCs are more sensitive to TGF-β1 than WT HSPCs. Sorted Lin− cells from WT or Fancd2−/− mice were exposed to TGF-β1. After 5 days in culture, LSK cells were analyzed by flow cytometry and quantified. Data are shown after normalizing to untreated WT group. (D) Representative immunoblots of the lysates from mouse fibroblast cells showing reduced phosphorylation of Smad2 by treatment with TGF-β inhibitors (TGF-beta 1,2,3 Ab and SD208). (E) TGF-beta 1,2,3 Ab and SD208 rescues inhibitory effect of TGF-β1 on bone marrow Lin− cell growth. Sorted Lin− cells from WT and Fancd2−/− mice were exposed to TGF-β1 (1 ng/mL) with or without TGF-beta 1,2,3 Ab (10 μg/mL) or SD208 (10 μM), and viable cells were counted after 5 days in culture. Data shown are after normalizing to untreated WT group. Error bars represent mean±s.e.m. (F) Clonogenic assay of WT and Fancd2−/− HSPCs treated with TGF-β1, TGF-beta 1, 2, 3 Ab or SD208. Equal number of sorted LSK cells from WT and Fancd2−/− mice were cultured in methylcellulose medium containing TGF-β1 (1 ng/mL), TGF-beta 1, 2, 3Ab (10 μg/mL), or SD208 (10 μM) in triplicate. Hematopoietic colonies were counted after 7-10 days in culture. Error bars represent mean±s.e.m. (G) Schematic of the experimental design for lentivirus shRNA transduction of Lin− bone marrow (BM) cells from WT and Fancd2−/− mice. (H) Representative immunoblots of the lysates from murine 3T3 cells showing knockdown efficiency of shRNA targeting mouse Smad3. (I) Representative FACS plots of LSK cells analyzed by flow cytometry for GFP expression after 5 days in vitro culture in stem cell culture medium. GFP+ or GFP− cells gated for LSK population are shown. (J) Representative FACS plots showing percentage of transduced donor derived cells in the peripheral blood samples of recipient mice at 4 and 16 weeks after bone marrow transplantation. The average percentages in each group were shown. (K) GM6914 (FA-A) cells exhibit higher TGFβ activity, compared to the FANCA corrected cells. GM6914 cells were transfected with TGFβ1-responsive luciferase promoter containing plasmid along with FANCA plasmid or empty vector and after 48 hrs. Luciferase activity was measured. (L) Binding of FANCD2 to SMAD1 promoter (region −2108 to −1950 bp) upon DNA damage as detected by ChIP assay using anti-FANCD2 antibody in corrected GM6914 (+FANCA) but not GM6914 (+Vector) fibroblast cells. Cells were exposed to MMC (1 μM) for 8 hrs before using them in ChIP assays with an anti-FANCD2 antibody or IgG control antibody, followed by real-time PCR. ChIP data are represented as enrichment fold of FANCD2 binding to the region after normalization with IgG.

Figure 16:
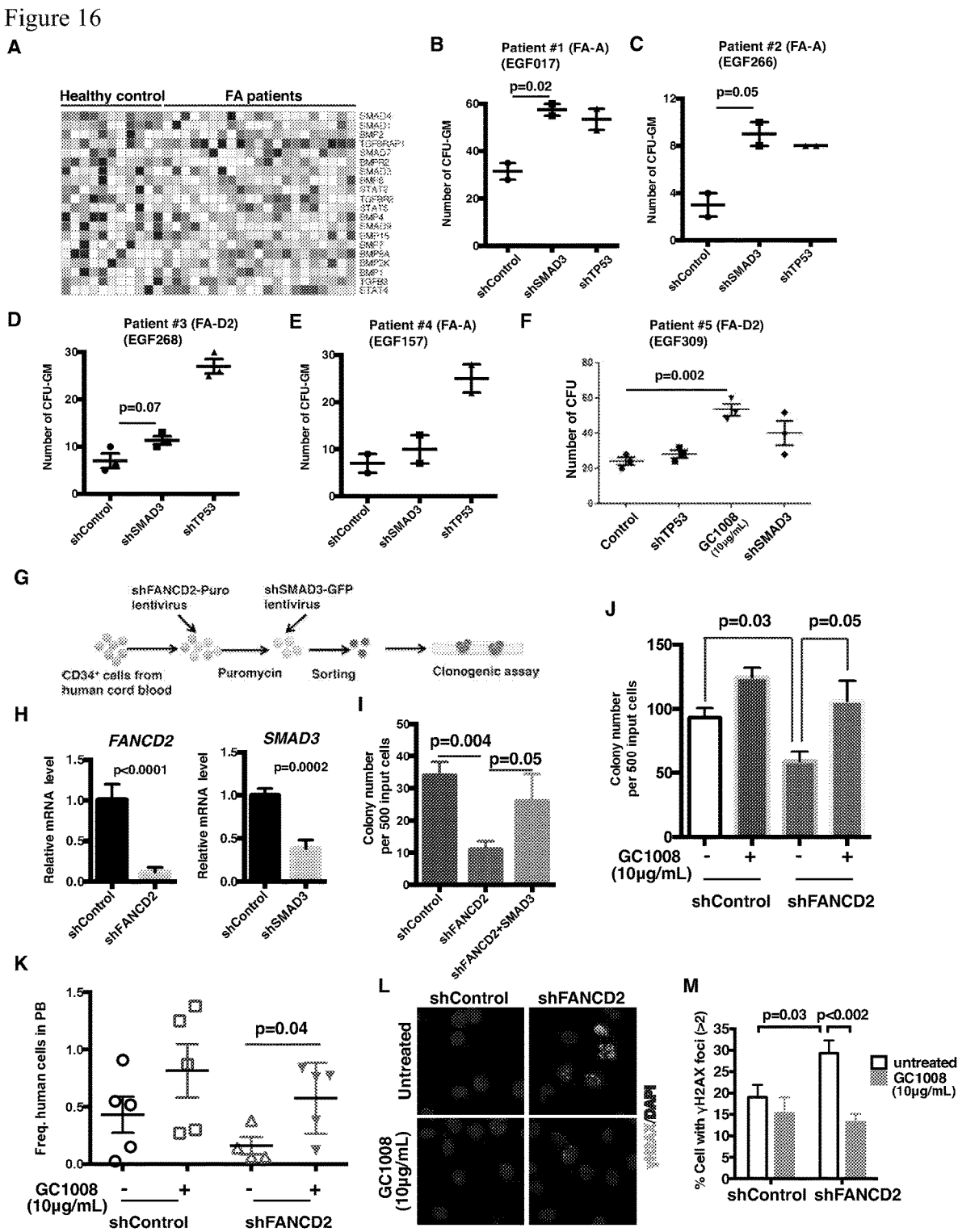

FIG. 16. TGF-β Pathway Blockade Rescues the Function of Primary HSPCs from Patients with FA.

(A) Hierarchical clustering and heat-map of the expression of TGF-β pathway genes in human FA and non-FA bone marrow samples using gene set enrichment analysis. (B-F) Colony forming assays using primary CD34+ bone marrow cells from five FA patients. Cells were transduced with lentiviruses encoding shControl, shTP53 or shSMAD3 followed by selection for puromycin resistance and then plated in methylcellulose cultures or the cells were directly plated in methylcellulose cultures containing GC1008 for colony growth. The hematopoietic colonies were counted after 10 days in culture. (G-I) Colony forming assays using FA-like CD34+ cells from human cord blood. As shown in the schematic (G), FA-like CD34+ cells were generated by transducing human cord blood CD34+ cells with lentivirus encoding shFANCD2. After selection for puromycin resistance, cells were transduced with lentivirus encoding shS- MAD3-GFP and GFP+ cells were sorted by FACS and subjected to clonogenic assay in triplicates. qRT-PCR analysis (H) shows significant reduction of FANCD2 and SMAD3 expression in cells. Hematopoietic colonies were counted after 10-14 days in culture (I). (J) Colony forming assay of FA-like CD34+ cells with GC1008 treatment. Hematopoietic colonies were counted after 10-14 days in culture. (K) In vivo xenograftment assay. Transduced human cord blood CD34+ cells with shFANCD2 or shControl were selected with puromycin and transplanted into sub-lethally irradiated NSG mice. Recipient mice were treated with GC1008 at 3 doses per week for 2 weeks. Human cells were analyzed in the peripheral blood at 2 weeks post transplantation. Data shown are combined from two independent experiments (n=4-5 recipient mice). (L,M) GC1008 rescues MMC-induced DNA damage in primary FA-like HSPCs. Representative images (L) and quantification (M) of γH2AX foci in cord blood CD34+ cells transduced with lentivirus encoding shFANCD2 or shControl. Puromycin resistant cord blood CD34+ cells transduced with lentivirus were exposed to MMC (100 ng/ml) for 2 hrs and allowed to recover for 24 hrs in presence of GC1008. Cells were then analyzed for γH2AX foci by immunofluorescence. Thirty to hundred cells with more than 5 foci were counted for each sample. Error bars represent mean±s.e.m. See also FIG. 18.

FIG. 17. TGF-β pathway Inhibition Increases HR and Decreases NHEJ activities in FA Cells.

(A, B) TGF-β pathway inhibition affects the choice of HR versus NHEJ pathways in repairing individual DNA breakpoints in FA cells. GM6914 cells (FA-A cells) or FANCA corrected GM6914 cells with shControl or shSMAD3 were used to generate traffic light reporter system, and then were infected with GFP-donor template and I-SceI lentivirus to generate DNA breakpoints. Quantification analysis of HR and NHEJ repair events is shown. (B) The ratio of HR to NHEJ activity based on the data in (A). (C) SD208 mediated TGF-β pathway inhibition increases HR events and decreases NHEJ events. Quantification of HR and NHEJ repair events in GM6914 cells exposed to SD-208 for 72 hrs as detected by traffic light reporter assay described in (A). (D) SMAD3 knockdown significantly increases HR efficiency. HR assay was measured in U2OS cells with DR-GFP reporter after transduction with lentivirus encoding indicated shRNAs. The representative of three independent experiments is presented. (E) NHEJ reporter assay showing decreased NHEJ activity in U2OS cells after inhibition of the TGF-β pathway by small molecule inhibitors. (F, G) TGF-β pathway inhibition promotes HR activity in FA cells. Representative images (F) and quantification (G) of RAD51 foci in MMC treated GM6914 (FA-A) cells or FANCA corrected GM6914 cells with shRNA-mediated knockdown of SMAD3. Cells were exposed to 1 μM MMC for 6 h, and allowed to recover for 24 h and 48 h. RAD51 foci were then identified. One hundred cells were scored for RAD51 foci. Error bars represent mean±s.e.m. See also FIG. 19.

FIG. 18. Inhibition of TGF-β Pathway Rescues Impaired Function of HSPCs from Patients with FA.

(A) Gene set enrichment analysis (GSEA) displays the expression profiling of TGF-β pathway genes in bone marrow cells from FA patients and healthy control. (Dataset: GSE16334). (B) Schematic of the clonogenic assay of primary CD34+ cells from FA patients. (C) Clonogenic survival of FA-like CD34+ cells exposed to MMC. Cells were cultured in methylcellulose medium post MMC treatment (2 h at 100 ng/mL) and hematopoietic colonies were counted after 10 days in culture. Colony numbers in each MMC treated group were normalized to untreated control of each group respectively. Error bars represent mean±s.e.m. (D) Colony forming assay of FA-like CD34+ cells. Human cord blood CD34+ cells expressing control shRNA or shFANCD2 were treated with GC1008 (10 μg/mL). for clonogenic assay in triplicates. Hematopoietic colonies were counted after 10-14 days in culture. Error bars represent mean±s.e.m. (E) In vivo xenograft assay. Human cord blood CD34+ cells were transduced with lentivirus encoding shFANCD2 or shControl. After selection with puromycin, cells were transplanted into sub-lethally irradiated NSG mice. Recipient mice were treated with GC1008 at 3 doses per week for 2 weeks. Human cells were analyzed in the peripheral blood by flow cytometry at 8 weeks post transplantation. Data shown are combined from two independent experiments (n=4-5 recipient mice). (F, GC1008 treatment promotes DNA repair in FA-like HSPCs. Human cord blood CD34+ cells expressing control shRNA or shFANCD2 were treated with MMC (100 ng/mL) for 2 h, and then allowed to recover for 24 h. Representative images (F) and quantification (G) of 53BP1 foci are shown.

Figure 19:
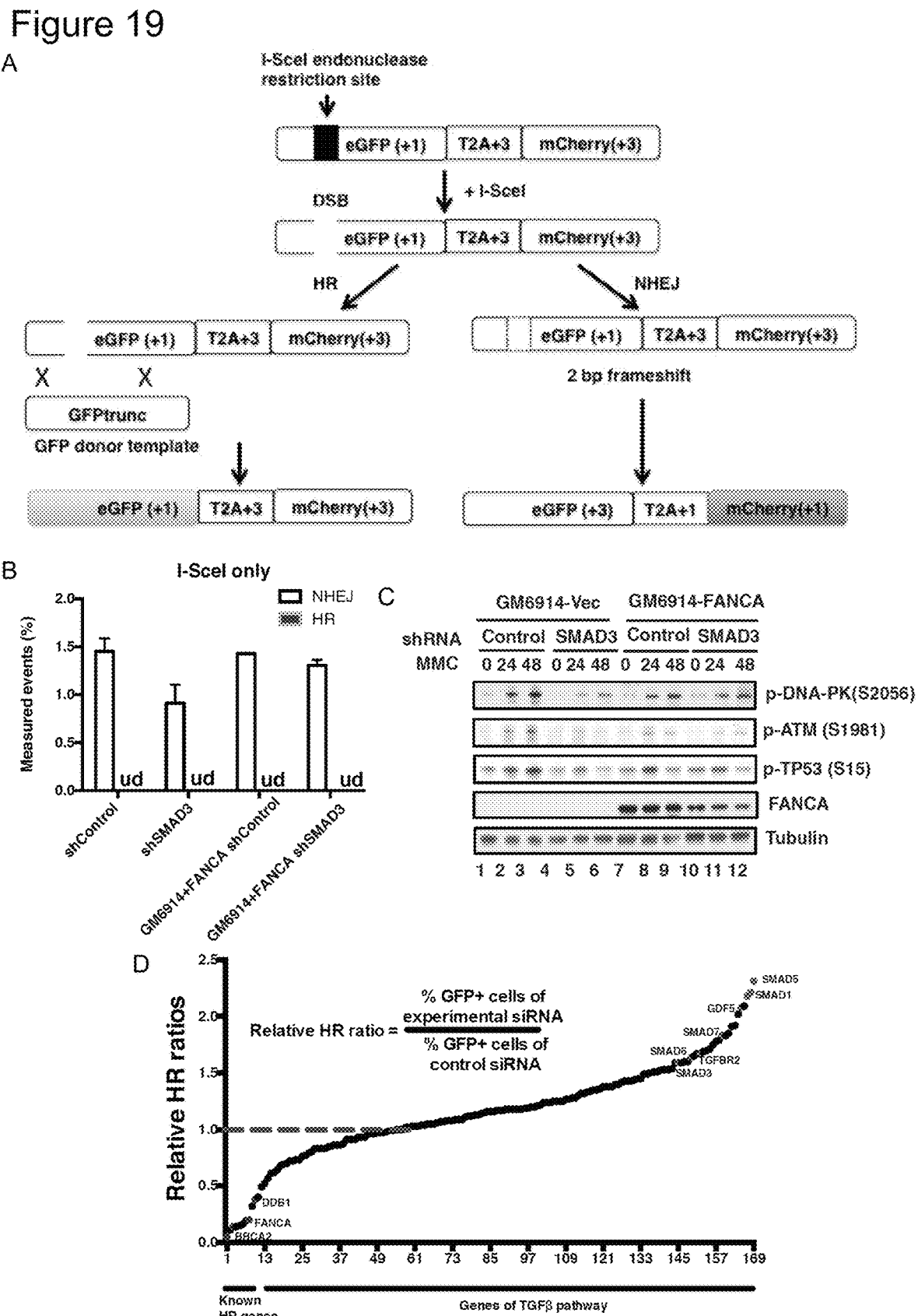

FIG. 19. Inhibition of TGF-β Pathway Increases HR Activity and Decreases NHEJ Activity in FA Cells.

(A) Schematic of traffic light reporter assay. Endonuclease I-SceI induces double strand break (DSB) in the restriction site. If the DSB is repaired by HR using truncated GFP template, the full eGFP gets reconstituted and cells are GFP-positive; if the DSB is repaired by NHEJ, 2 bp frameshift leads to T2A and mCherry sequences in frame, and cells are mCherry-positive. (B) HR and NHEJ repair analyzed by traffic light reporter (TLR) system. GM6914 (FA-A cells) or FANCA corrected GM6914 cells with shControl or shSMAD3 were infected with lentivirus encoding TLR-BFP reporter and were then infected with and I-SceI only encoding lentivirus to generate DNA breakpoints. HR and NHEJ repair events (GFP or mCherry positive cells) were quantified by flow cytometry. (C) Immunoblots with the indicated antibodies of the lysates from GM6914 (FA-A) cells or FANCA-corrected GM6914 cells with shRNA-mediated knockdown of SMAD3. Cells were exposed to 1 μM MMC for 8 h and allowed to recover for 24 and 48 hours. (D) Analysis of siRNA screening data showing that siRNA mediated knockdown of the majority of the TGF-β pathway genes enhances HR efficiency. [siRNA screening database was used from Adamson et al., A genome-wide homologous recombination screen identifies the RNA-binding protein RBMX as a component of the DNA-damage response. *Nature Cell Biology*, 14: 318-328 (2012)].

DETAILED DESCRIPTION OF THE INVENTION

The invention is based in part upon the surprising discovery that inhibition of the TGF β signaling pathway will rescue the growth of bone marrow cells in patients with Fanconi Anemia (FA).

More specifically, it was discovered that blocking the transforming growth factor β (TGFβ) pathway, by either genetic deletion or pharmacologic inhibition, significantly enhanced FA cellular growth and improved cellular survival in the presence of DNA interstrand crosslinking agents.

Blocking the TGF-β pathway improves the survival of FA cells and rescues the proliferative and functional defects of HSPCs derived from FA mice and FA patients. Inhibition of TGF-β signaling in FA HSPCs results in elevated homologous recombination (HR) repair with a concomitant decrease in non-homologous end-joining (NHEJ), accounting for the improvement in cellular growth.

In humans, three isoforms of TGFβ, TGFβ1, TGFβ2 and TGFβ3, are known to exist. (Swiss Prot accession numbers P001137, P08112 and P10600 (respectively)). In their biologically active state, these three isoforms are 25 kDa homodimers comprising two 112 amino acid monomers joined by an inter-chain disulfide bridge. TGFβ1 differs from TGFβ2 by 27 amino acids, and from TGFβ3 by 22 amino acids. The differences are mainly conservative amino acid changes. The three-dimensional structure of TGFβ has been determined by X-ray crystallography and the receptor binding regions have been defined. Both human TGFβs and mouse TGFβs are similar. The human TGFβ1 has one amino acid difference from a mouse TGFβ1. Human TGFβ2 has only a three amino acid difference from mouse TGFβ2, and human and mice TGFβ3 are identical.

Bone marrow stromal cells derived from Fancd2-deficient mouse exhibited hyperactive noncanonical TGFβ-Erk pathway, and inhibition of this pathway also restored resistance to genotoxic agents. Moreover, inhibition of the canonical TGFβ-Smad pathway rescued the proliferation defect of hematopoietic stem/progenitor cells (HSPCs) from Fancd2-deficient mice and human FA patients. Mechanistically, hyperactive TGFβ signaling in FA cells resulted in elevated non-homologous end joining (NHEJ) activity and reduced homologous recombination (HR) repair. The activation of HR repair by TGFβ inhibition accounts, at least in part, for the improvement in cellular growth. Taken together, inhibition of the TGFβ signaling pathway will provide a therapeutic strategy in the clinical treatment of FA patients with bone marrow failure.

Despite the elucidation of the FA/BRCA pathway[2,3], the pathophysiological mechanism of BMF in FA has remained elusive. Research has been hampered by the fact that FA pathway-deficient mice do not spontaneously develop bone marrow failure[12]. Recent studies have demonstrated that HSPCs from FA patients and FA mice have a hyperactive p53/p21 axis, resulting, at least in part, in the increased BMF[9]. The hyperactivation of p53/p21 appears to result from unresolved DNA replication stress, endogenous DNA damage, and other cellular stresses. The progressive impairment of HSPC by p53-mediated cell cycle arrest and apoptosis also accounts for the observed delay in onset of BMF in FA patients.

Here, we describe a novel mechanism for BMF in FA patients and mouse models—namely, the hyperactivation of the TGFβ pathway in FA HSPCs and stromal bone marrow fibroblasts. Using an unbiased shRNA screen, we initially identified hyperactive components of the TGFβ signaling pathway, which suppress the growth of FA patient-derived cell lines. Inhibition of TGFβ pathway, in HSPCs and in primary bone marrow stromal cells, partially rescued the growth and crosslinker hypersensitivity of these cells. Knockdown of TGFβ pathway signaling proteins, such as SMAD3 of the canonical pathway, and MEK and pERK1/2 of the non-canonical pathway, led to enhanced FA cellular growth. Additionally, FA cells display hypersensitivity to many inflammatory cytokines[7,8]. Elevated TGFβ1 level, secreted by bone marrow stromal cells and hematopoietic cells, suppresses HSPCs in FA bone marrows, and subsequently leads to bone marrow failure. Recent studies demonstrated that a dysfunctional bone marrow niches can lead to the development of hematopoietic malignancies[43,44], and TGFβ1 released from bone marrow stromal cells can promote the clonal evolution myeloid leukemias[45]. Our data further establish the role of bone marrow microenvironment in the pathogenesis of BMF of FA through hyperactivation of TGFβ pathway. The mechanism by which TGFβ pathway is activated in FA remains unknown. Previous studies demonstrated that FA pathway is involved in the regulation of cytokine generation. For instance, FANCC has been implicated IFNγ signaling through interacting with HSP70 and STAT1[46,47]. Whether TGFβ production is regulated by the FA pathway will require further investigation.

TGFβ Inhibitors

Accordingly, the invention provides methods of treating, preventing or delaying the onset of bone marrow failure in Fanconi Anemia patients by administering to a subject in need thereof a TGFβ inhibitor.

A TGFβ inhibitor is a compound that decreases expression or activity of TGFβ inhibitor. A decrease in TGFβ inhibitor activity is defined by a reduction of a biological function of TGFβ inhibitor. A TGFβ inhibitor can neutralize TGFβ, interfere with binding of TGFβ to its receptor or inhibits a component of the TGFβ signaling pathway such as SMAD3, MEK or pERK1/2.

The TGFβ inhibitor can be a small molecule. A "small molecule" as used herein, is meant to refer to a composition that has a molecular weight in the range of less than about 5 kD to 50 daltons, for example less than about 4 kD, less than about 3.5 kD, less than about 3 kD, less than about 2.5 kD, less than about 2 kD, less than about 1.5 kD, less than about 1 kD, less than 750 daltons, less than 500 daltons, less than about 450 daltons, less than about 400 daltons, less than about 350 daltons, less than 300 daltons, less than 250 daltons, less than about 200 daltons, less than about 150 daltons, less than about 100 daltons. Small molecules can be, e.g., nucleic acids, peptides, polypeptides, peptidomimetics, carbohydrates, lipids or other organic or inorganic molecules. For example, the small molecule TGFβ inhibitor is a DNA dependent protein kinase inhibitor, a SMAD3 inhibitor, a TGFβR1 inhibitor or a MEK1/2 inhibitor.

A DNA dependent protein kinase inhibitor includes for example, Compound 401, DMNB, KU 0060648, NU 7026, NU 7441, or PI 103 hydrochloride.

A SMAD3 inhibitor includes for example SIS3 or naringenin.

A TGFβR1 inhibitor includes for example, Galunisertib, YR-290, SB431542 SB525334, SD208, LY2109761, SB431542, SB525334, SB505124, GW788388, LY364947, LY2109761, RepSox, or EW-7197. Preferably the TGFβR1 inhibitor is Galunisertib A MEK1/2 inhibitor includes for example, U0126, PD98059, PD0325901, PD184352, PD318088, SL327, AZD8330, U0126-EtOH, PD318088, Trametinib, Pimasertib, AZD8330, or Binimetinib.

The TGFβ inhibitor is an antibody or fragment thereof specific to TGFβ or TGFβR1. Methods for designing and producing specific antibodies are well-known in the art.

The TGFβ inhibitor is for example an antisense TGFβ nucleic acid, a TGFβ-specific short-interfering RNA, or a TGFβ-specific ribozyme. Alternatively, the TGFβ inhibitor is for example an antisense SMAD3 nucleic acid, a SMAD3-specific short-interfering RNA, or a SMAD3-specific ribozyme. By the term "siRNA" is meant a double stranded RNA molecule which prevents translation of a target mRNA. Standard techniques of introducing siRNA into a cell are used, including those in which DNA is a template from which an siRNA is transcribed. The siRNA includes a sense TGFβ or SMAD3 nucleic acid sequence, an anti-sense TGFβ or SMAD3 nucleic acid sequence or both. Optionally, the siRNA is constructed such that a single transcript has both the sense and complementary antisense sequences from the target gene, e.g., a hairpin (shRNA). Optionally, the siRNA is constructed as a short guided RNA (sgRNA). Examples of siRNAs shRNAs and sgRNA are disclosed in the examples herein.

Binding of the siRNA to a TGFβ or SMAD3 transcript in the target cell results in a reduction in TGFβ or SMAD3 production by the cell. The length of the oligonucleotide is at least 10 nucleotides and may be as long as the naturally-occurring TGFβ or SMAD3 transcript. Preferably, the oligonucleotide is 19-25 nucleotides in length. Most preferably, the oligonucleotide is less than 75, 50, 25 nucleotides in length.

Therapeutic Methods

Bone marrow failure is treated, prevented or delayed, by administering to a subject having Fanconi Anemia a TGFβ inhibitor. In other aspects, the TGFβ inhibitor is administered to a subject that is to receive a bone marrow transplant.

Treatment is efficacious if the treatment leads to clinical benefit such as, an increase in bone marrow stems cells and/or bone marrow stromal fibroblast cells in the patient. When treatment is applied prophylactically, "efficacious" means that the treatment retards or prevents bone marrow failure or alleviates a clinical symptom of bone marrow failure such as decreasing blood count. Efficaciousness is determined in association with any known method for diagnosing or treating bone marrow failure.

The TGFβ inhibitor is administered before the patient is prepared for a bone marrow transplant, after a bone marrow transplant or both. Alternatively, the compound is administered after the patient is prepared for a bone marrow transplant but before the bone marrow transplant. By prepared for a bone marrow transplant is meant that the paint has had undergone a conditioning regimen such a chemotherapy, total body irradiation, or both to weaken or destroy the unhealthy bone marrow.

In other embodiments the TGFβ inhibitor is administered to subject during a medical crisis such as a bacterial or viral infection.

Therapeutic Administration

The invention includes administering to a subject composition comprising a TGFβ inhibitor.

An effective amount of a therapeutic compound is preferably from about 0.1 mg/kg to about 150 mg/kg. Effective doses vary, as recognized by those skilled in the art, depending on route of administration, excipient usage, and coadministration with other therapeutic treatments including use of other therapeutic agents for treating, preventing or alleviating bone marrow failure such as androgen therapy or erythropoietin.

A therapeutic regimen is carried out by identifying a mammal, e.g., a human patient suffering from Fanconi Anemia by standard methods.

Doses may be administered once, or more than once. In some embodiments, it is preferred that the therapeutic compound is administered once a week, twice a week, three times a week, four times a week, five times a week, six times a week, or seven times a week for a predetermined duration of time, most preferably 3 times per week although less frequent dosing may be preferred if targeting the blood compartment as in Fanconia Anemia. The predetermined duration of time may be 1 week, 2 weeks, 3 weeks, 4 weeks, 5 weeks, 6 weeks, 7 weeks, 2 months, 3 months, 4 months, 5 months, 6 months, 7 months, 8 months, 9 months, 10 months, 11 months, or up to 1 year, preferably for 1 to two months. In some cases, chronic administration may be desired, especially in the treatment of a condition lasting more than three months like Fanconia Anemia. The terms "chronic administration" or "administered chronically" mean prolonged drug administration for a duration of greater than three months.

The predetermined duration of time may be 1 week, 2 weeks, 3 weeks, 4 weeks, 5 weeks, 6 weeks, 7 weeks, 2 months, 3 months, 4 months, 5 months, 6 months, 7 months, 8 months, 9 months, 10 months, 11 months, or up to 1 year.

The pharmaceutical compound is administered to such an individual using methods known in the art. Preferably, the compound is administered orally, rectally, nasally, topically or parenterally, e.g., subcutaneously, intraperitoneally, intramuscularly, and intravenously. Preferably the compound is administered intravenously. The inhibitors are optionally formulated as a component of a cocktail of therapeutic drugs. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for other routes of administration utilizing conventional methods. For example, the therapeutic compounds are formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, conventional filler, and a tableting agent. Other formulations include an ointment, suppository, paste, spray, patch, cream, gel, resorbable sponge, or foam. Such formulations are produced using methods well known in the art.

Therapeutic compounds are effective upon direct contact of the compound with the affected tissue. Accordingly, the compound is administered topically. Alternatively, the therapeutic compounds are administered systemically. For example, the compounds are administered by inhalation. The compounds are delivered in the form of an aerosol spray from pressured container or dispenser which contains a suitable propellant, e.g., a gas such as carbon dioxide, or a nebulizer.

Additionally, compounds are administered by implanting (either directly into an organ or subcutaneously) a solid or resorbable matrix which slowly releases the compound into adjacent and surrounding tissues of the subject.

Definitions

The term "TGFβ" or "transforming growth factor-beta" refers to the family of molecules described that have either the full-length, native amino acid sequence of any of the humans TGFβ isoforms.

A "TGFβ antibody" refers to an antibody or antigen binding fragment thereof that binds to any of the isoforms of TGFβ, preferably binding to either TGFβ1, TGFβ2, or TGFβ3, or to any combination thereof.

The term "polypeptide" refers, in one embodiment, to a protein or, in another embodiment, to protein fragment or fragments or, in another embodiment, a string of amino acids. In one embodiment, reference to "peptide" or "polypeptide" when in reference to any polypeptide of this invention, is meant to include native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminal, C terminal or peptide bond modification, including, but not limited to, backbone modifications, and residue modification, each of which represents an additional embodiment of the invention. Methods for preparing peptidomimetic compounds are well known in the art and are specified, for example, in Quantitative Drug Design, C. A. Ramsden Gd., Chapter 17.2, F. Choplin Pergamon Press (1992).

As used interchangeably herein, the terms "oligonucleotides", "polynucleotides", and "nucleic acids" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, all as described herein.

The term "homology", when in reference to any nucleic acid sequence indicates a percentage of nucleotides in a candidate sequence that are identical with the nucleotides of a corresponding native nucleic acid sequence. Homology may be determined by computer algorithm for sequence alignment, by methods well described in the art. For example, computer algorithm analysis of nucleic acid or amino acid sequence homology may include the utilization of any number of software packages available, such as, for example, the BLAST, DOMAIN, BEAUTY (BLAST Enhanced Alignment Utility), GENPEPT and TREMBL packages.

As used herein, the term "substantial sequence identity" or "substantial homology" is used to indicate that a sequence exhibits substantial structural or functional equivalence with another sequence. Any structural or functional differences between sequences having substantial sequence identity or substantial homology will be de minimus; that is, they will not affect the ability of the sequence to function as indicated in the desired application. Differences may be due to inherent variations in codon usage among different species, for example. Structural differences are considered de minimus if there is a significant amount of sequence overlap or similarity between two or more different sequences or if the different sequences exhibit similar physical characteristics even if the sequences differ in length or structure. Such characteristics include, for example, the ability to hybridize under defined conditions, or in the case of proteins, immunological crossreactivity, similar enzymatic activity, etc. The skilled practitioner can readily determine each of these characteristics by art known methods.

Additionally, two nucleotide sequences are "substantially complementary" if the sequences have at least about 70 percent or greater, more preferably 80 percent or greater, even more preferably about 90 percent or greater, and most preferably about 95 percent or greater sequence similarity between them. Two amino acid sequences are substantially homologous if they have at least 50%, preferably at least 70%, more preferably at least 80%, even more preferably at least 90%, and most preferably at least 95% similarity between the active, or functionally relevant, portions of the polypeptides.

To determine the percent identity of two sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

Thus, treating may include suppressing, inhibiting, preventing, treating, delaying the onset of or a combination thereof. Treating refers inter alia to increasing time to sustained progression, expediting remission, inducing remission, augmenting remission, speeding recovery, increasing efficacy of or decreasing resistance to alternative therapeutics, or a combination thereof "Suppressing" or "inhibiting", refers inter alia to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. The symptoms are primary, while in another embodiment, symptoms are secondary. "Primary" refers to a symptom that is a direct result of the proliferative disorder, while, secondary refers to a symptom that is derived from or consequent to a primary cause. Symptoms may be any manifestation of a disease or pathological condition.

As used herein, "an ameliorated symptom" or "treated symptom" refers to a symptom which approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" or "therapeutic amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

The terms "patient" "subject" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

By the term "modulate," it is meant that any of the mentioned activities, are, e.g., increased, enhanced, increased, augmented, agonized (acts as an agonist), promoted, decreased, reduced, suppressed blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values, for example, 1-fold, 2-fold, 3-fold, 5-fold, 10-fold, 100-fold, etc.

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

EXAMPLES

Example 1: General Methods

Whole Genome Pooled shRNA Screen

The screen was performed essentially as previously described (Luo J. et al, 2009 Cell). The Hannon-Elledge whole genome pooled shRNA library consists of six viral pools each containing approximately 13,000 different MSCV-PM retroviral shRNA particles targeting human genes. For each pool, three replicates of at least $1.3 \times 10^7$ GM6914 cells were incubated with an equivalent number of retroviral colony-forming units in media containing 8 µg/ml polybrene (Sigma-Aldrich, St. Louis, MO), for a 1000-fold representation of each shRNA sequence at a multiplicity-of-infection (MOI) of 1. Puromycin (2 µg/ml) was added to the cells 24 hours post transduction and maintained for 48 hours for selection of stable integrants. Cells were treated with MMC 19 nM for 7 days, and surviving cells were washed and cultured for 2 additional weeks. Genomic DNA was extracted from cells harvested both before and after MMC treatment. Half-hairpin shRNA-containing sequences were amplified by PCR. An equal amount of input genomic DNA for each sample was used. For each sample, we performed 8 separate 100 µL reactions, and then combined the resulting amplicons. Primer sequences to recover half-hairpin shRNA in the first PCR reaction are:

```
JH353F
                                        (SEQ ID NO: 1)
5'-TAGTGAAGCCACAGATGTA-3'

HHR2L
                                        (SEQ ID NO: 2)
5'-ATGTATCAAAGAGATAGCAAGGTATTCAG-3'
```

Two more PCR reactions were performed to attach Illumina adaptors and barcodes. Primer sequences are as follows:

```
IndexSeqPrimer(ISP)-shRNAloop:
                                        (SEQ ID NO: 3)
5'-GTGACTGGAGTTCAGACGTGTGCTCTTCCGATCTtagtgaagccac
agatgta-3'

P7-IndexingPrimer:
                                        (SEQ ID NO: 4)
5'-CAAGCAGAAGACGGCATACGAGAT[xxxxxxx]GTGACTGGAGTTC
AGACGTGT-3'

P5-HHR2L:
                                        (SEQ ID NO: 5)
5'-AATGATACGGCGACCACCGAatgtatcaaagagatagcaaggtatt
cag-3'
```

Resulting amplicons were gel extracted, quantified, mixed and sequenced using Illumina HiSeq2000.

Data Processing and Initial Analysis

To align the sequences with the reference shRNA sequence library, bowtie was used with the following parameters:

bowtie -p 2 -best -nomaqround -norc -trim3 28 -k 1 -n 0 -v 2 -a <path to the base-name of the reference files> $i <output filename>

To collate and count the hairpins, grep and awk was used. To normalize the values, the R package DESeq was used to perform TMM normalization. To compare the abundances of shRNA integrants pre and post MMC treatment, the log 2 fold change of the mean of the replicates was determined for each hairpin. To rank genes, RIGER was used using the pre-scored option.

Animals

We generated Fancd2$^{-/-}$ mice as previously described[12]. C57BL/6J-CD45.1, and C57BL/6J-CD45.2 mice were obtained from mice were purchased from The Jackson Laboratory. All mice were in C57BL/6J background, and were bred and maintained in a temperature- and humidity-controlled environment and given unrestricted access to 6% chow diet and acidified water. We treated WT and Fancd2$^{-/-}$ mice with 0.3 mg/kg MMC to induce bone marrow failure. Animal experiments were performed following the approved protocol of the Animal Care and Use Committee at the Dana Farber Cancer Institute.

Cell Culture and Protein Techniques

Human 293T, U2OS, and FA cells, including GM6914, PD20, DF1653.B, DF1238.B, DF117.B, FHCC-P5, FHCC-73, FHCC-42E, and FHCC196A, were cultured in Dulbecco's Modified Eagle's Medium (Life Technologies) supplemented with 10% fetal calf serum (FBS). Human FA cells EUFA316 were grown in RPMI1640 (Life Technologies) supplemented with 10% fetal calf serum. Fancd2$^{+/+}$ and Fancd2$^{-/-}$ bone marrow stromal cells were established by culturing whole bone marrow in DMEM with 10% FBS. Fancd2$^{-/-}$ stromal cells were complemented with human FANCD2 by retroviral transduction of FANCD2 cDNA in pMMP-PURO vector, followed by selection in puromycin. Whole cell extracts were prepared by lysing cells in radio-immunoprecipitation assay buffer (50 mmol/L Tris, pH 7.3, 150 mmol/L NaCl, 1 mmol/L EDTA, 1% Triton X-100, 0.5% Na-deoxycholate, and 0.1% SDS) with complete protease inhibitor, NaVO4, and NaF.

Antibodies and Reagents

The following antibodies were used for western blotting: p-ERK1/2 (Santa Cruz), p-SMAD2/3 (Cell Signaling), SMAD3 (Cell Signaling), TGF-βR1 (Santa Cruz), p53 (Cell Signaling), p21 (Santa Cruz), p-p38 (Cell Signaling), p38 (Cell Signaling), p-JNK1/2 (Cell Signaling), p-JNK1/2 (Cell Signaling), RAD51 (Santa Cruz), p-DNA-PK (abcam) Vinculin (Santa Cruz), Tubulin (Cell Signaling). DNA-PK inhibitor NU7026 and SMAD3 inhibitor SIS3 were purchased from EMD Millipore, and TGF-βR1 inhibitor LY364947, SD208, MEK1/2-inhibitor PD0325901 were from Sigma. Recombinant human TGFβ1, SCF, TPO, IGF, and bFGF were from ProPeptide, and Mouse TGFβ1 from R&D.

shRNA and CRISPR Construction

Lentiviral shRNA vector pLKO.1 were obtained from RNAi Core facility of Dana Farber Cancer Institute. Sequences of SMAD3 and TP53 shRNA were as follows:

```
shRNA-SMAD3:
                                        (SEQ ID NO: 6)
5'-CTGTGTGAGTTCGCCTTCAAT-3':

shRNA-TP53:
                                        (SEQ ID NO: 7)
5'-CGGCGCACAGAGGAAGAGAAT-3'
```

CRISPRs were designed at crispr.mit.edu provided by the Zhang laboratory and then cloned into pLenti-CRISPR/Cas9 vector (Addgene) following Zhang's protocol (genome-engineering.org/gecko/?page_id-15). The target sequences were as follows: Smad3: GTTCACGTTCTGCGTGGTGA (SEQ ID NO: 8); p53: AGGAGCTCCTGACACTCGGA (SEQ ID NO: 9); Tgfbr1: ATGAGGAGCTGCGGACGACG (SEQ ID NO: 10).

Lentivirus Production and Transduction.

To produce lentivirus, HEK293T cells were seeded at ~50% confluence 24 hours before transfection. Transfection was performed using LTX and plus reagent (Life Technologies). Virus was harvested 48 hours post transfection, and filtered through a 0.45 µm low protein binding membrane (Millipore). To transduce human FA cells and bone marrow stromal cells, an MOI of about 0.5 was used. To transduce bone marrow cells from WT and Fancd2$^{-/-}$ mice, Lin$^-$ cells were isolated using EasySep™ stem cell enrichment kit (StemCell Technology) and transduced with lentivirus at MOI of 8-10.

Hematopoietic Stem/Progenitor Cell Culture and Flow Cytometry Analysis.

For mouse hematopoietic stem/progenitor cell culture, Lin$^-$ cells were cultured in vitro in StemSpan SFEM media with 10 ng/mL SCF, 20 ng/mL IGF-2, 20 ng/mL TPO, 10 ng/mL heparin, and 10 ng/mL α-FGF. Half media was changed every three days. For human cord blood cells, CD34$^+$ cells were isolated using CD34 microbead kit (Miltenyi Biotec). Cells were cultured in StemSpan SFEM media with 100 ng/mL hSCF, 100 ng/mL FLT3 ligand, 10 ng/mL TPO, 10 ng/mL IL-6.

To perform flow cytometry analysis, Lin$^-$ cells were collected at day 2 and 5 post transduction and suspended in staining medium (PBS with 2% heat-inactivated calf serum), and incubated with PE-conjugated c-Kit and APC-conjugated Sca-1 antibodies were added to the cells for 30 min at 4° C. in the dark. Stem cell population (GFP$^+$Lin$^-$c-Kit$^+$Sca-1$^+$) was analyzed by FACS. All these antibodies were purchased from eBioscience.

Functional Cell-Based Assays

For survival assays, cells were seeded at a density of $1\times10^3$ cells per well in 96-well plates. After 72 hours of culture in indicated concentrations of MMC or post exposure of acetaldehyde, viability was assessed using CellTiterGlo reagent (Promega). In order to assess clonogenicity, cells were seeded at a low density (500-1000 cells per well) in 6-well plates and allowed to form colonies. The cells were then fixed in methanol/20% acetic acid and stained with 1% crystal violet. Colony formation was assessed by solubilizing crystal violet stain with methanol and quantifying UV absorbance for each condition.

ELISA

Cell culture supernatant were harvested, and the TGFβ1 level was assessed using TGF-β1 Multispecies ELISA Kit (Invitrogen) following the manual procedure.

Immunofluorescence

Cells were grown on coverslip for 24 hours before treated with MMC. Cells were fixed with 4% (w/v) paraformaldehyde for 10 min at room temperature, washed three times with PBS, followed by extraction with 0.3% Triton X-10 for 10 min on ice. The incubation with the primary antibody (anti-RAD51, Santa Cruz) was done at 37° C.

Comet Assay

To evaluate MMC induced DNA cross-link damage and repair, a modified alkaline Comet assay was performed[37,38]. Briefly, cells were seeded into 6-well plates at 20% confluence and treated with MMC for 6 hours, and washed and release for 24 and 48 hours. Cells were collected, placed on slide coated with agarose, and lysed according to manufacturer's protocol of Trevigen's Comet Assay Kit (Trevigen). After lysis, the slides were irradiated to induce strand breaks with 5 Gy γ-radiation. Electrophoresis was conducted, and comets were visualized using an Axio Imager Z1 fluorescence microscope with an AxioCam MRm CCD camera (Zeiss, Thornwood, NY).

Real Time RT-PCR

Total RNA was isolated using the RNeasy Mini kit (Qiagen, CA). cDNA was synthesized using High-Capacity cDNA Reverse Transcription Kit (Life Technologies). All real time PCR reactions were done using Vii A 7 PCR machine. 20 µL reaction system was composed of 10 µL SYBR Green, 2.5 µL 20 uM primer mixture, 10 ng cDNA and nuclease-free water. All experiments were performed in triplicate. Gapdh was the internal control. The primer sequences were shown as follows: Tgfb1 sense: CAGCTCCTCATCGTGTTGGTG (SEQ ID NO: 11); Tgfb1 antisense: GCACATACAAATGGCCTGTCTC (SEQ ID NO: 12); Smad3 sense: CACGCAGAACGTGAACACC (SEQ ID NO: 13); Smad3 antisense: GGCAGTAGA-TAACGTGAGGGA (SEQ ID NO: 14); Gapdh sense: TGGATTTGGACGCATTGGTC (SEQ ID NO: 15); Gapdh antisense: TTTGCACTGGTACGTGTTGAT (SEQ ID NO: 16).

Murine Bone Marrow Transplantation

Donor cells (CD45.2$^+$) were transplanted into lethally irradiated (10 Gy dose) recipient (congenic B6-CD45.1$^+$ mice) along with $1\times10^5$ cells competitive bone marrow cells from congenic B6-CD45.1$^+$ mice. Peripheral blood from recipient mice was analyzed for donor cell engraftment as described (Parmar et al., 2010).

Colony-Forming Unit-Spleen (CFU-S) Assay

Recipient mice (wild-type, 8-12 weeks old) were irradiated with a split dose of 1100 rad (550 rad each, 4 hours apart) before transplantation. Forty thousand bone marrow cells from donor mice were transplanted into each recipient mouse. Ten to 12 days post-transplantation, spleens were harvested and fixed with Bouin fixative solution.

In Vivo Xenograft Assay

Human cord blood derived CD34$^+$ cells were transduced with lentivirus encoding shFANCD2 or shControl as described (Ceccaldi et al., 2012). While cells were selected with 2 µg/mL puromycin, cells were also treated with 10 µg/mL GC1008. After 48 h treatment, $2\times10^5$ cells were transplanted into sub-lethally irradiated (2.5 Gy) NSG mice. The recipient mice were treated with 10 mg/kg GC1008 at 3 doses per week for two weeks. Two and eight weeks after transplantation, human cells in peripheral blood (PB) were analyzed using anti-human CD45 antibody (eBioscience, 17-0459-42) by flow cytometry.

TGF-β Pathway Activity Using Luciferase Reporter Assay 293T cells were transiently transfected with a TGF-β responsive luciferase promoter (CAGA-luc) plasmid (kindly provided by H.Y. Lin, Massachusetts General Hospital) along with FANCD2 or control vector. Cells were harvested at 48 h after transfection and luciferase activity was determined using the Dual-Luciferase Reporter Assay system (Promega).

Traffic Light Reporter (TLR) Assay

Genome engineering experiments were performed as previously described (Certo et al., 2011). Briefly, single copy of TLR cell lines including FANCA–/– fibroblast cells (GM6914) and FANCA corrected GM6914 with or without shSMAD3 were generated by transducing cells with TLR-BFP reporter lentivirus, typically yielding ~5% transduction based on fluorescence. Two days after transduction, transduced cells (BFP+) were sorted by FACS. To generate double strand break, cells were seeded at 2×105 cells per well in 6-well plate 24 h before transduction, and cells were transduced with lentivirus containing I-SceI alone or I-SceI plus GFP donor template. For SD208 treatment, cells were treated with 10 μM SD208 after 3-4 h post-transduction. All transductions were carried out in the presence of 8 μg/mL polybrene. Twenty-four hours after transduction, medium was changed. Genome engineering events were analyzed by flow cytometry at 72 hours after transduction. NHEJ is represented by mCherry fluorescence, and HR by GFP fluorescence.

Drug Sensitivity Assays

For survival assays, cells were seeded at a density of 1×103 cells per well in 96-well plates. After 3-6 days of culture in indicated concentrations of MMC or post exposure of acetaldehyde, viability was assessed using CellTiterGlo reagent (Promega). In order to assess clonogenicity, cells were seeded at a low density (500-1000 cells per well) in 6-well plates and allowed to form colonies. The cells were then fixed in methanol/20% acetic acid and stained with 1% crystal violet. Colonies were counted after crystal violet staining.

Chromatin Immunoprecipitation (ChIP) Assay

The ChIP assay was performed as described previously (Park et al., 2013). Briefly, 10×106 cells were treated with MMC (1 μM) for 8 hours. Cells were chemically crosslinked with 1% formaldehyde for 15 min at room temperature. Cells were rinsed twice with 1×PBS and harvested in Farnham lysis buffer (5 mM PIPES pH8.0, 85 mM KCl, 0.5% NP-40, and protease inhibitor cocktail). After washing, cells were resuspended in sonication buffer (PBS, 1% NP-40, 0.5% sodium deoxycholate, 0.1% SDS, and protease inhibitor cocktail), and sonicated with 10×30 seconds pulses, 5 min in total, 18-21 Watts of power. After sonication, 5% samples were used as input. Sonicated samples were further divided in half, and incubated overnight with 100 μL of Dynal Protein G magnetic beads that had been preincubated with anti-FANCD2 (Novus Biologicals, NB100-316) or IgG control antibody. Beads were washed 5× with LiCl wash buffer (100 mM Tris pH 7.5, 500 mM LiCl, 1% NP-1% sodium deoxycholate), and 1×TE buffer containing 50 mM NaCl. Bound complexes were eluted from the beads by heating at 65° C. for 1 hour (vortexing every 5 min). Crosslinking was reversed by incubating samples at 65° C. for overnight. DNA was purified and then analyzed by real-time PCR using SMAD1 promoter primers (primer #1: 5' AAGGCAGGAGAATTGCTTGA-3', 5'-CCTT-CACCTTCTGCCATGAT-3'; primer #2: 5'-CAAGG-GAGGGTTTCAACAG-3', 5'-TGAGCACTTACTGGT-CAATTCG-3').

Statistics

Two-tailed P values for statistical analysis were obtained using Student's t-test.

Example 2: TGFB Pathway Blockade Enhances FA Cell Survival in the Presence of Genotoxic Agents Initially, we performed a whole genome-wide shRNA screen in FANCA-deficient human fibroblasts in order to identify genes whose knockdown would rescue the FA phenotype. Specifically, shRNAs were identified that enhance the colony growth of a patient-derived FANCA[-/-] cell line in the presence of the crosslinking agent, mitomycin C (MMC). The shRNA library consisted of six pools, each containing approximately 13,000 different MSCV-PM retroviral shRNA sequences targeting human genes[25]. Transduced cells were selected in puromycin and exposed to a concentration of MMC that killed 90% of the parental FA cells (FIGS. 7A and B). shRNA inserts were PCR-amplified from MMC-selected cells using primers with barcodes, and next generation sequencing was used for decoding shRNA hairpins. The relative abundance of shRNAs between untreated cells and surviving cells post MMC treatment was compared. Cells bearing shRNAs that conferred resistance were enriched from the treated population.

Interestingly, multiple targets of the TGFβ pathway were among the top hits after RIGER analysis of the data (FIG. 1A). Multiple shRNA oligos directed against p53 were also enriched in surviving cells from the treated population, consistent with our previous studies indicating that p53 knockdown can rescue FA hematopoietic defects[9]. We next validated our primary screening data through knocking down SMAD3 in the same FA cells used in the screen. shRNA knockdown of SMAD3 significantly enhanced survival of FA cells in the presence of MMC (FIG. 1B, and FIG. 7C). The effect of TGFβ pathway on genotoxin-induced growth suppression was further validated using other FA cell lines and known TGFβ pathway inhibitors (FIGS. 1C and D, and FIG. 7D). siRNA-mediated knockdown of SMAD3 and pharmacologic inhibition of the TGFβ pathway with small molecules, such as SD208[26] and SIS3[27], improved FA cells survival in the presence of MMC (FIGS. 1C and D, and FIG. 7D), but do not significantly alter cytotoxicity of corrected FA cells.

Recent studies indicated that DNA damaged by an endogenous crosslinking agent, acetaldehyde, requires the FA pathway for repair[28]. We identified an FA patient-derived lymphoblast line, EUFA316, is hypersensitive to acetaldehyde (FIG. 7E). Both pharmacologic inhibition by SD208 and genetic deletion by shRNA-mediated knockdown of the TGFβ pathway significantly promoted survival of these cells in the presence of acetaldehyde (FIGS. 1E and F). Since elevated p53 reduces the growth and upregulates apoptosis in FA cells[9], we also tested whether TGFβ pathway knockdown results in a secondary decline in the cellular levels of p53 or p21 (a p53 target protein). Knockdown of the TGFβ pathway by shRNA or by small molecule inhibitors resulted in reduced expression of p53 and p21 (FIG. 1G). Together, these data revealed that TGFβ pathway plays an important role in the growth inhibition of FA cells induced by genotoxic agents, and inhibition of this pathway can rescue the survival of FA cells.

Example 3: Bone Marrow Stromal Cells Exhibit a Hyperactive Non-Canonical TGFB-ERK Pathway Previous studies have suggested that bone marrow stromal fibroblasts, from human FA patients and FA pathway-deficient mouse models, are hypersensitive to genotoxic stress and have impaired growth[29, 13]. In order to examine the role of the bone marrow stromal cells in FA pathogenesis, we established primary bone marrow stromal cells from the Fancd2[-/-] mouse (FIG. 2)[30]. As expected, Fancd2[-/-] stromal cells exhibited MMC hypersensitivity, MMC-induced chromosome radials, and a growth and clonogenic defect (FIG. 2A and FIG. 8A-C). Interestingly, multiple independent FA stromal cell populations, from FA patients or from FA mouse models exhibited elevated levels of pERK1/2, but not p-p38 and pJnk1/2 (FIGS. 8D and E).

Previous studies have indicated that hyperactivity of the non-canonical TGFβ pathway can increase pERK levels through activation of the upstream kinase, MEK[24]. We therefore hypothesized that primary FA stromal cells secrete a TGFβ or TGFβ-related cytokine that promotes TGFβ pathway activity via an autocrine mechanism. To evaluate TGFβ activation in FA-deficient stromal cells, TGFβ expression in conditioned media from FA lines was examined by ELISA. FA murine stromal cells showed elevated serum level of mTGFβ1, correlating with their heightened Tgfb1 mRNA levels (FIG. 2B). Importantly, mTGFβ1 exposure further activated pErk1/2 in FA stromal cells (FIG. 2C). To further explore the possibility that TGFβ is responsible for elevated ERK activation in FA stromal cells, we targeted TGFβ pathway by either CRISPR-Cas9-sgRNA mediated deletion of Tgfbr1 or small molecule inhibitors. Interestingly, both knockdown of Tgfbr1 and treatment with a small molecule inhibitor of TGFβ significantly reduced pErk levels (FIGS. 2C and D). Together, these data indicate that the hyperactive TGFβ pathway activates pErk in FA stromal cells through the non-canonical signaling pathway.

Example 4: Inhibition of the Non-Canonical TGFB Pathway Enhances FA Cellular Growth The MEK inhibitor, PD0325901 blocks MEK-induced phosphorylation of pERK1/2[31]. We reasoned that this inhibitor might rescue the phenotypes of FA-deficient stromal cells. To test this hypothesis, mouse stromal cells were exposed to the inhibitor and analyzed for pErk expression. Treatment with PD0325901 resulted in the inhibition of Erk1/2 phosphorylation, and significantly increased the clonogenicity of Fancd2$^{-/-}$ stromal cells (FIGS. 3A and B, and FIG. 9). Since Fancd2$^{-/-}$ stromal cells are sensitive to MMC (FIG. 2A), we assessed whether deletion of TGFβ pathway could rescue their MMC sensitivity. We deleted Tgfbr1 in Fancd2$^{-/-}$ stromal cells using the CRISPR-Cas9 system. As control, we also knocked down p53 (FIG. 3C). As expected, deletion of Tgfbr1 in Fancd2$^{-/-}$ stromal cells caused MMC resistance similar to the resistance observed following p53 deletion (FIG. 3D). CRISPR-Cas9-mediated knockdown of Smad3 in Fancd2$^{-/-}$ stromal cells did not rescue MMC sensitivity, indicating that the canonical TGFβ-SMAD pathway is less relevant to the growth defect of FA stromal cells. Taken together, these findings demonstrate that targeting the non-canonical TGFβ-Erk pathway in FA bone marrow stromal cells can reduce genotoxic stress-mediated growth inhibition.

Example 5: Inhibition of the Canonical TGFB Pathway Promotes the Proliferation of Primary Murine Hematopoietic Stem and Progenitor Cell We next tested for the expression of TGFβ pathway transcripts in early hematopoietic stem and progenitor cells (FIG. 4). Whole bone marrow cells were isolated from wild type (WT) and Fancd2$^{-/-}$ mice, and exposed to a range of concentrations of MMC. Genotoxic stress strongly activated TGFβ-SMAD pathway, resulting higher pSmad2 expression in the Fancd2$^{-/-}$ cells following MMC treatment (FIG. 4A). Quantitative RT-PCR on hematopoietic stem/progenitor cell enriched Lin$^-$Sca-1$^+$c-Kit$^+$ (LSK) population and Lin$^-$ cells from either WT or Fancd2$^{-/-}$ mice was performed. Elevated mRNA expression of both Tgfβ1 and Smad3 mRNA transcripts in the LSK population from the Fancd2$^{-/-}$ mice was observed, as well as higher expression of Tgfβ1 alone in Fancd2$^{-/-}$ Lin$^-$ cells (FIG. 4B). pErk activation was not detected in the Fancd2$^{-/-}$ hematopoietic cells (FIG. 10A). Bone marrow HSPCs from Fancd2−/− mice exhibit growth defects when cultured in vitro[12,13]. We therefore transduced Lin− cells, from either WT or Fancd2$^{-/-}$ mice, with a GFP-lentiviral shRNA targeting Smad3 (FIG. 4C and FIG. 10B). GFP-positive cells were analyzed after 2 and 5 days in culture for the percentage of LSK cells in the population. Interestingly, Smad3 knockdown strongly promoted LSK expansion in the Fancd2$^{-/-}$ population (FIG. 4D-E, FIG. 10B). Together, these data demonstrate that TGFβ expression is elevated in murine Fancd2$^{-/-}$ HSPCs due to genotoxic stress, and inhibition of the canonical TGFβ-Smad pathway can restore their proliferation defects.

Example 7: The TGFB Pathway is Hyperactive in Primary Bone Marrow Cells of FA Patients and TGFB Pathway Inhibition Restores Clonogenic Capability of Human FA CD34$^+$ Cells To confirm that FA patients have constitutive activation of the TGFβ pathway in the HSPCs in vivo, we evaluated gene expression in fresh bone marrow samples of FA patients versus healthy donors (FIG. 6A and FIG. 11A). Consistent with our shRNA screen, FA bone marrow cells demonstrated increased mRNA expression of TGFβ pathway components. We further examined whether blocking TGF pathway restores the function of FA hematopoietic stem/progenitor cells by measuring the clonogenic ability of CD34+ progenitor cells from FA patients. Interestingly, we found knockdown of SMAD3 significantly rescues hematopoietic progenitor clonogenic defects of primary FA bone marrow, which is comparable to those of p53 knockdown cells (FIG. 6B and FIG. 11B). Together, our data indicate that TGFβ pathway inhibition restores the function of human FA CD34$^+$ cells.

Example 8: Inhibition of the TGFB Pathway in FA Cells Promotes DNA Repair Activity Recent studies suggest that TGFβ signaling affects cellular activity of DNA repair. First, Kirshner et al[33] demonstrated that hyperactivation of TGFβ signaling activates the DNA damage response, resulting in upregulation of activated (phosphorylated) ATM, Chk2, and p53. Second, hyperactivation of the TGFβ pathway may activate the NHEJ DNA repair pathway. Other studies indicate that FA cells have elevated pATM and NHEJ[33,34], perhaps resulting from hyperactive TGFβ signaling. Third, TGFβ signaling can suppress homologous recombination DNA repair. Accordingly, TGFβ inhibition can activate HR repair and enhance reprogramming of inducible pluripotent stem cells (iPS cells) 35,36. Since TGFβ inhibitors rescue FA cell growth, we hypothesized that the mechanism entails cellular alterations in DNA repair. To test this hypothesis, we initially set up a modified crosslink comet assay to assess the level of MMC induced DNA damage in FANCA-deficient fibroblasts. In this assay[37,38,26], the length of comet tail was negatively correlation with MMC doses (FIGS. 12A and B). Interestingly, through this assay, SMAD3 knockdown partially rescued crosslink repair, almost to the level of wild-type FANCA complementation (FIG. 7A).

We next tested whether inhibition of the TGFβ pathway in FA cells can rescue HR accounting for the improvement in FA cellular growth. DR-GFP assay is a well known assay for HR repair[39]. Knockdown of SMAD3 resulted in increased HR activity (FIG. 7B and FIG. 12C), supporting this hypothesis. To extend these studies, we used another template reporter assay which measures the cellular activity of competing DNA repair pathway, NHEJ[40]. Interestingly, knockdown of the TGFβ pathway with the small molecule inhibitors, SD208 or SIS3, decreased NHEJ (FIG. 7C).

To further implicate the TGFβ pathway in DNA repair modulation, we examined the formation of RAD51 foci. FANCA-deficient cells exposed to shSMAD3 or corrected with FANCA, displayed much higher level of RAD51 foci after MMC treatment (FIGS. 7D and E), compared to parental FA cells. In contrast to the increased level of RAD51 foci in parental FA cells, after recovery for 24 h and 48 h, RAD51 foci quickly decreased in SMAD3 knockdown cells and FANCA corrected cells, implying that DNA damage is reducing during recovery in these cells. These data indicate that inhibition of TGF pathway increases homologous recombination activity.

To further elucidate the molecular mechanism, we focused on DNA damage response signaling. As expected, MMC strongly activated DNA damage response signaling in FA cells, including increased phosphorylation of ATM and p53. Hyperactivation of these signaling events was observed at 48 h, indicating the persistence of damaged DNA in these cells. However, DNA damage response signaling significantly diminished in SMAD3-depleted FA cells or corrected FA cells after 48 h post MMC treatment. Deletion of SMAD3 caused a decrease in phosphorylation of DNA-PK (S2056) in FA cells after MMC treatment (FIG. 7F). Treatment with TGFβ inhibitors SD208 and SIS3 gave similar results, and TGFβ1 activated phosphorylation of DNA-PK (FIGS. 12D and E). These data are consistent with previous studies indicating that NHEJ factors inhibit the processing of DSBs by blocking the recruitment of HR factors, resulting in MMC hypersensitivity[41,42]. Taken together, inhibition of TGFβ pathway promotes the repair of DNA damage of FA cells and partially rescues genotoxic agent-induced DNA interstrand crosslinks.

Example 9: TGF-β Pathway Inhibition Rescues the Functional Defects of HSCs from FA Mice As FA mice exhibit HSPC defects, the possible suppressive function of the TGF-β pathway in bone marrow HSPCs of FA mice was next examined. Elevated expression levels of both Tgfb1 and Smad3 were observed in Fancd2$^{-/-}$ HSPCs [Lin$^-$Sca-1$^+$c-Kit$^+$ (LSK) population] (FIG. 14A). Elevated pSmad2/3 protein levels were also observed in Fancd2$^{-/-}$ HSPCs (FIGS. 15A and 15B). Moreover, enhanced mRNA expression of TGF-β pathway target genes, including Cdkn1a, Cdkn1c, Foxp3, and Atg5, was also observed in Fancd2$^{-/-}$ HSPCs (FIG. 14A), implying that the TGF-β pathway is upregulated in FA HSPCs. Fancd2$^{-/-}$ bone marrow HSPCs were more sensitive to TGF-β1 than wild-type HSPCs (FIG. 15C). Therefore, we hypothesized that inhibition of this pathway might rescue the defect of FA HSPCs. Colony forming assays showed that the clonogenic ability of Fancd2$^{-/-}$ HSPCs was inhibited by TGF-β1; blockade of the TGF-β signaling by a neutralizing antibody against mouse TGF-β (Brenet et al., 2013) or SD208 markedly enhanced the clonogenic ability (FIG. 15D-15F). Further, genetic knockdown of Smad3 promoted the in vitro expansion of HSPCs and in vivo engraftment of Lin$^-$ cells from bone marrow of Fancd2$^{-/-}$ mice (FIGS. 14B, 14C, and 15G-15J). Taken together, inhibition of the TGF-β pathway can rescue the functional defects of Fancd2$^{-/-}$ HSPCs.

Hyperactive TGF-β pathway signaling in Fancd2$^{-/-}$ HSPCs prompted us to assess whether the FA pathway components directly transcriptionally regulate the expression of TGF-β pathway genes. We first confirmed that mutation in FA genes results in hyperactive TGF-β activity. We transfected a TGF-β luciferase reporter vector containing SMAD binding element, into FA cells or corrected FA cells. Interestingly, increased TGF-β luciferase activity was observed in FA-A cells compared to FANCA-corrected cells (FIG. 15K). Conversely, overexpression of FANCD2 in 293T cells significantly reduced the TGF-β luciferase reporter activity (FIG. 14D). Using chromatin immunoprecipitation (ChIP) assays, we previously showed that activated FANCD2 increases the transcriptional activity of the TAp63 gene (Park et al., 2013). A genome-wide ChIP sequencing (ChIP-seq) analysis, using FANCD2 antibody, demonstrated that FANCD2 also binds to SMAD gene promoters (Park et al., 2013). ChIP confirmed that FANCD2 can directly bind to the promoter region of a SMAD gene, suggesting that FANCD2 decreases the transcriptional activity of SMAD genes. Interestingly, FANCD2 bound to the promoter of SMAD1 in 293T cells (FIG. 14E). The binding of FANCD2 to the promoter of SMAD1 was observed in corrected FA cells, but not in the parental FA cells (EUFA316 and GM6914), suggesting that a functional FA pathway is required for the FANCD2-mediated transcriptional decrease of the TGFβ pathway gene (FIGS. 14F and 15L). Collectively, these results demonstrate that disruption of the FA pathway causes transcriptional changes, resulting in hyperactive TGF-β signaling.

Example 10 TGF-B Pathway Inhibition Restores the Function of HSPCS Derived from Humans with FA We next extended our studies in HSPCs derived from patients with FA. Primary human FA bone marrow cells demonstrated increased mRNA expression of multiple TGF-β pathway components (FIGS. 16A and 18A). TGF-β pathway inhibition, by knockdown of SMAD3 or by exposure to anti-human TGF-β neutralizing antibody GC1008, rescued the clonogenic defects of primary HSPCs from bone marrow of FA patients, although to a lesser extent than the rescue observed following p53 knockdown (FIGS. 16B-16F and 18B). Variable response to TGF-β pathway inhibition in primary human FA patient HSPCs may result from differences in the age, gender, intrinsic genetic differences, the levels of SMAD3/p53 in HSPCs, or the severity of the pre-existing bone marrow failure. Depletion of SMAD3 in FA-like primary HSPCs established by FANCD2 knockdown in human cord blood CD34$^+$ cells, also rescued their clonogenicity, and partially restored MMC resistance (FIGS. 16G-16I and 18C). Inhibition of TGF-β signaling by GC1008 also recapitulated this phenotype by markedly rescuing the clonogenic capacity of FA-like HSPCs (FIGS. 16J and 18D). Further, since the very low CD34$^+$ cell numbers in FA patients did not allow efficient xenograft assays for analysis of clonogenicity in vivo, we performed a surrogate in vivo xenograft assay using FA-like CD34$^+$ cells. Strikingly, GC1008 treatment in vivo enhanced the engraftment of primary FA-like CD34$^+$ cells (FIGS. 16K and 18E). In addition, we observed a higher frequency of FA-like HSPCs with γH2AX and 53BP1 foci upon MMC exposure, compared to the control HSPCs (FIGS. 16L, 16M, 18F and 18G). Exposure to GC1008 significantly reduced the number of FA-like HSPCs with γH2AX and 53BP1 foci (FIGS. 16L, 16M, 18F and 18G), suggesting that TGF-β pathway inhibition improves DNA repair in these primary human FA-like HSPCs. Together, our data indicate that the TGF-β signaling is increased in human FA HSPCs and that blockade of this pathway partially restores their function.

Example 11: TGF-β Pathway Inhibition Increases HR and Decreases NHEJ in FA Cells To directly confirm that inhibition of TGF-β pathway modulates HR or NHEJ activity, we engineered an individual DNA breakpoint in FA (GM6914) cells and employed the traffic light reporter (TLR) system which quantifies both HR and NHEJ activities (Certo et al., 2011). In the TLR assay, double strand break (DSB) generated by I-Sce1 endonuclease can be repaired by either HR or NHEJ pathway when the donor repair template is provided, however, the DSB can be repaired by NHEJ only when the repair template is missing (FIG. 19A). NHEJ and not HR activity was observed in FA cells when the donor repair template was missing (FIG. 19B), validating the assay. As predicted, FA (GM6914) cells exhibited fewer HR events compared to the FA-A-corrected (GM6914+FANCA) cells (FIG. 17A). Interestingly, TGF-β pathway inhibition, by knockdown of SMAD3, in FA cells resulted in increased HR events with a concomitant decrease in NHEJ events (FIGS. 17A and 17B). Inhibition of TGF-β pathway by the small molecule inhibitor SD208 also resulted in increased HR activity in FA cells (FIG. 17C). Similar findings were revealed when different reporter systems were used to quantify the HR and NHEJ activities individually (FIGS. 17D and 17E). Consistently, knockdown of SMAD3 in FA cells resulted in decreased phosphorylation of DNA-PK, a marker of NHEJ (FIG. 19C). Additionally, damage-induced RAD51 foci resolved more quickly in SMAD3-depleted FA cells (FIGS. 17F and 17G), implying that HR-mediated DNA repair is more efficient in these cells. Analysis of the genome-wide siRNA screening data (Adamson et al., 2012) revealed that siRNA-mediated knockdown of several TGF-β pathway genes enhanced HR activity (FIG. 19D). Taken together, these data indicate that TGF-β pathway inhibition promotes DNA repair by directly increasing HR activity in FA cells.

REFERENCES

1. Shimamura, A. & Alter, B. P. Pathophysiology and management of inherited bone marrow failure syndromes. *Blood reviews* 24, 101-122 (2010).
2. Kottemann, M. C. & Smogorzewska, A. Fanconi anaemia and the repair of Watson and Crick DNA cross-links. *Nature* 493, 356-363 (2013).
3. Deans, A. J. & West, S. C. DNA interstrand crosslink repair and cancer. Nat Rev *Cancer* 11, 467-480 (2011).
4. Chan, K. L., Palmai-Pallag, T., Ying, S. & Hickson, I. D. Replication stress induces sister-chromatid bridging at fragile site loci in mitosis. *Nat Cell Biol* 11, 753-760 (2009).
5. Naim, V. & Rosselli, F. The FANC pathway and BLM collaborate during mitosis to prevent micro-nucleation and chromosome abnormalities. *Nat Cell Biol* 11, 761-768 (2009).
6. Vinciguerra, P., Godinho, S. A., Parmar, K., Pellman, D. & D'Andrea, A. D. Cytokinesis failure occurs in Fanconi anemia pathway-deficient murine and human bone marrow hematopoietic cells. *J Clin Invest* 120, 3834-3842 (2010).
7. Pang, Q. & Andreassen, P. R. Fanconi anemia proteins and endogenous stresses. *Mutat Res* 668, 42-53 (2009).
8. Dufour, C., et al. TNF-alpha and IFN-gamma are overexpressed in the bone marrow of Fanconi anemia patients and TNF-alpha suppresses erythropoiesis in vitro. *Blood* 102, 2053-2059 (2003).
9. Ceccaldi, R., et al. Bone marrow failure in Fanconi anemia is triggered by an exacerbated p53/p21 DNA damage response that impairs hematopoietic stem and progenitor cells. *Cell stem cell* 11, 36-49 (2012).
10. Crossan, G. P., et al. Disruption of mouse Slx4, a regulator of structure-specific nucleases, phenocopies Fanconi anemia. *Nature genetics* 43, 147-152 (2011).
11. Pulliam-Leath, A. C., et al. Genetic disruption of both Fancc and Fancg in mice recapitulates the hematopoietic manifestations of Fanconi anemia. *Blood* 116, 2915-2920 (2010).
12. Parmar, K., et al. Hematopoietic stem cell defects in mice with deficiency of Fancd2 or Usp1. *Stem Cells* 28, 1186-1195 (2010).
13. Zhang, Q. S., et al. Fancd2−/− mice have hematopoietic defects that can be partially corrected by resveratrol. *Blood* 116, 5140-5148 (2010).
14. Tulpule, A., et al. Knockdown of Fanconi anemia genes in human embryonic stem cells reveals early developmental defects in the hematopoietic lineage. *Blood* 115, 3453-3462 (2010).
15. Ito, K., et al. Reactive oxygen species act through p38 MAPK to limit the lifespan of hematopoietic stem cells. *Nature medicine* 12, 446-451 (2006).
16. Ruzankina, Y., et al. Deletion of the developmentally essential gene ATR in adult mice leads to age-related phenotypes and stem cell loss. *Cell stem cell* 1, 113-126 (2007).
17. Niedernhofer, L. J. DNA repair is crucial for maintaining hematopoietic stem cell function. *DNA Repair (Amst)* 7, 523-529 (2008).
18. Mohrin, M., et al. Hematopoietic stem cell quiescence promotes error-prone DNA repair and mutagenesis. *Cell stem cell* 7, 174-185 (2010).
19. Milyaysky, M., et al. A distinctive DNA damage response in human hematopoietic stem cells reveals an apoptosis-independent role for p53 in self-renewal. *Cell stem cell* 7, 186-197 (2010).
20. Seita, J., Rossi, D. J. & Weissman, I. L. Differential DNA damage response in stem and progenitor cells. *Cell stem cell* 7, 145-147 (2010).
21. Brenet, F., Kermani, P., Spektor, R., Rafii, S. & Scandura, J. M. TGFbeta restores hematopoietic homeostasis after myelosuppressive chemotherapy. *J Exp Med* 210, 623-639 (2013).
22. Zhou, L., et al. Reduced SMAD7 leads to overactivation of TGF-beta signaling in MDS that can be reversed by a specific inhibitor of TGF-beta receptor I kinase. *Cancer Res* 71, 955-963 (2011).
23. Zingariello, M., et al. Characterization of the TGF-beta1 signaling abnormalities in the Gata1 low mouse model of myelofibrosis. *Blood* 121, 3345-3363 (2013).
24. Ikushima, H. & Miyazono, K. TGFbeta signalling: a complex web in cancer progression. *Nat Rev Cancer* 10, 415-424 (2010).
25. Cron, K. R., et al. Proteasome inhibitors block DNA repair and radiosensitize non-small cell lung cancer. *PLoS One* 8, e73710 (2013).
26. Zhou, L., et al. Inhibition of the TGF-beta receptor I kinase promotes hematopoiesis in MDS. *Blood* 112, 3434-3443 (2008).
27. Jinnin, M., Ihn, H. & Tamaki, K. Characterization of SIS3, a novel specific inhibitor of Smad3, and its effect on transforming growth factor-beta1-induced extracellular matrix expression. *Molecular pharmacology* 69, 597-607 (2006).

28. Garaycoechea, J. I., et al. Genotoxic consequences of endogenous aldehydes on mouse haematopoietic stem cell function. *Nature* 489, 571-575 (2012).

29. Li, Y., et al. Mesenchymal stem/progenitor cells promote the reconstitution of exogenous hematopoietic stem cells in Fancg–/– mice in vivo. *Blood* 113, 2342-2351 (2009).

30. Epperly, M. W., et al. Increased longevity of hematopoiesis in continuous bone marrow cultures and adipocytogenesis in marrow stromal cells derived from Smad3(–/–) mice. *Exp Hematol* 33, 353-362 (2005).

31. Jessen, W. J., et al. MEK inhibition exhibits efficacy in human and mouse neurofibromatosis tumors. *J Clin Invest* 123, 340-347 (2013).

32. Langevin, F., Crossan, G. P., Rosado, I. V., Arends, M. J. & Patel, K. J. Fancd2 counteracts the toxic effects of naturally produced aldehydes in mice. *Nature* 475, 53-58 (2011).

33. Kirshner, J., et al. Inhibition of transforming growth factor-beta1 signaling attenuates ataxia telangiectasia mutated activity in response to genotoxic stress. *Cancer Res* 66, 10861-10869 (2006).

34. Kennedy, R D., et al. Fanconi anemia pathway-deficient tumor cells are hypersensitive to inhibition of ataxia telangiectasia mutated. *J Clin Invest* 117, 1440-1449 (2007).

35. Ichida, J. K., et al. A small-molecule inhibitor of tgf-Beta signaling replaces sox2 in reprogramming by inducing nanog. *Cell stem cell* 5, 491-503 (2009).

36. Lin, T., et al. A chemical platform for improved induction of human iPSCs. *Nat Methods* 6, 805-808 (2009).

37. Wu, J. H. & Jones, N. J. Assessment of DNA interstrand crosslinks using the modified alkaline comet assay. *Methods Mol Biol* 817, 165-181 (2012).

38. McKenna, D. J., Gallus, M., McKeown, S. R., Downes, C. S. & McKelvey-Martin, V. J. Modification of the alkaline Comet assay to allow simultaneous evaluation of mitomycin C-induced DNA cross-link damage and repair of specific DNA sequences in RT4 cells. *DNA Repair (Amst)* 2, 879-890 (2003).

39. Nakanishi, K., et al. Human Fanconi anemia monoubiquitination pathway promotes homologous DNA repair. *Proceedings of the National Academy of Sciences of the United States of America* 102, 1110-1115 (2005).

40. Mansour, W. Y., et al. Hierarchy of nonhomologous end-joining, single-strand annealing and gene conversion at site-directed DNA double-strand breaks. *Nucleic acids research* 36, 4088-4098 (2008).

41. Adamo, A., et al. Preventing nonhomologous end joining suppresses DNA repair defects of Fanconi anemia. *Mol Cell* 39, 25-35 (2010).

42. Pace, P., et al. Ku70 corrupts DNA repair in the absence of the Fanconi anemia pathway. *Science* 329, 219-223 (2010).

43. Raaijmakers, M. H., et al. Bone progenitor dysfunction induces myelodysplasia and secondary leukaemia. *Nature* 464, 852-857 (2010).

44. Hanoun, M., et al. Acute myelogenous leukemia-induced sympathetic neuropathy promotes malignancy in an altered hematopoietic stem cell niche. *Cell stem cell* 15, 365-375 (2014).

45. Krause, D. S., et al. Differential regulation of myeloid leukemias by the bone marrow microenvironment. *Nature medicine* 19, 1513-1517 (2013).

46. Pang, Q., et al. The Fanconi anemia protein FANCC binds to and facilitates the activation of STAT1 by gamma interferon and hematopoietic growth factors. *Molecular and cellular biology* 20, 4724-4735 (2000).

47. Pang, Q., Keeble, W., Christianson, T. A., Faulkner, G. R. & Bagby, G. C. FANCC interacts with Hsp70 to protect hematopoietic cells from IFN-gamma/TNF-alpha-mediated cytotoxicity. *EMBO journal* 20, 4478-4489 (2001).

48. Benazet, J. D., et al. Smad4 is required to induce digit ray primordia and to initiate the aggregation and differentiation of chondrogenic progenitors in mouse limb buds. *Development* 139, 4250-4260 (2012).

49. Li, J., et al. TNF-alpha induces leukemic clonal evolution ex vivo in Fanconi anemia group C murine stem cells. *J Clin Invest* 117, 3283-3295 (2007).

50. Bunting, S. F. & Nussenzweig, A. Dangerous liaisons: Fanconi anemia and toxic nonhomologous end joining in DNA crosslink repair. *Mol Cell* 39, 164-166 (2010).

51. Grafe, I., et al. Excessive transforming growth factor-beta signaling is a common mechanism in osteogenesis imperfecta. *Nature medicine* 20, 670-675 (2014).

We claim:

1. A method of expanding hematopoietic stem/progenitor cells obtained from a patient having Fanconi Anemia (FA), the method comprising contacting a population of hematopoietic stem/progenitor cells with a compound that inhibits the expression or activity of TGFβ, wherein the compound is 1) an antibody that is specific for TGFβ or TGFβR1, or 2) a nucleic acid that is a short hairpin RNA (shRNA), a small interfering RNA (siRNA), or a single guide RNA (sgRNA) specific for SMAD3.

2. The method of claim 1, wherein the compound is a nucleic acid that is an shRNA, siRNA or an sgRNA specific for SMAD3.

3. The method of claim 1, wherein the compound is an antibody that is specific for TGFβ or TGFβR1.

4. The method of claim 2, wherein the compound is a nucleic acid that is an shRNA.

5. The method of claim 2, wherein the compound is a nucleic acid that is an siRNA.

6. The method of claim 5, wherein the siRNA binds to a SMAD3 transcript in a target cell.

7. The method of claim 2, wherein the compound is a nucleic acid that is an sgRNA specific for SMAD3.

8. The method of claim 3, wherein the compound is an antibody that is specific for TGFβ.

9. The method of claim 3, wherein the compound is an antibody that is specific for TGFβR1.

10. The method of claim 1, wherein the method of expanding occurs in vitro.

11. The method of claim 1, wherein the method of expanding occurs in vivo.

12. The method of claim 1, wherein the population of hematopoietic stem/progenitor cells is obtained from a patient's bone marrow.

13. The method of claim 12, wherein the hematopoietic stem/progenitor cells are Lin-hematopoietic stem/progenitor cells.

14. The method of claim 1, wherein the hematopoietic stem/progenitor cells are CD34+ cells.

15. An in vitro method of expanding hematopoietic stem/progenitor cells comprising contacting a population of hematopoietic stem/progenitor cells obtained from bone marrow of a patient having Fanconi Anemia (FA) with a compound that inhibits the expression or activity of TGFβ, wherein the compound is 1) an antibody that is specific for TGFβ or TGFβR1, or 2) a nucleic acid that is a short hairpin RNA (shRNA), a small interfering RNA (siRNA), or a single guide RNA (sgRNA) specific for SMAD3.

16. The method of claim 15, wherein the compound is a nucleic acid that is an shRNA, siRNA or an sgRNA specific for SMAD3.

17. The method of claim 16, wherein the compound is a nucleic acid that is an shRNA.

18. The method of claim 16, wherein the compound is a nucleic acid that is an siRNA.

19. The method of claim 18, wherein the siRNA binds to a TGFβ or SMAD3 transcript in a target cell.

* * * * *

SEQUENCE LISTING

```
Sequence total quantity: 16
SEQ ID NO: 1              moltype = DNA  length = 19
FEATURE                   Location/Qualifiers
source                    1..19
                          mol_type = other DNA
                          organism = Synthetic construct
SEQUENCE: 1
tagtgaagcc acagatgta                                        19

SEQ ID NO: 2              moltype = DNA  length = 29
FEATURE                   Location/Qualifiers
source                    1..29
                          mol_type = other DNA
                          organism = Synthetic construct
SEQUENCE: 2
atgtatcaaa gagatagcaa ggtattcag                             29
```

-continued

```
SEQ ID NO: 3            moltype = DNA   length = 53
FEATURE                 Location/Qualifiers
source                  1..53
                        mol_type = other DNA
                        organism = Synthetic construct
SEQUENCE: 3
gtgactggag ttcagacgtg tgctcttccg atcttagtga agccacagat gta          53

SEQ ID NO: 4            moltype = DNA   length = 52
FEATURE                 Location/Qualifiers
source                  1..52
                        mol_type = other DNA
                        organism = Synthetic construct
SEQUENCE: 4
caagcagaag acggcatacg agatnnnnnn ngtgactgga gttcagacgt gt           52

SEQ ID NO: 5            moltype = DNA   length = 49
FEATURE                 Location/Qualifiers
source                  1..49
                        mol_type = other DNA
                        organism = Synthetic construct
SEQUENCE: 5
aatgatacgg cgaccaccga atgtatcaaa gagatagcaa ggtattcag              49

SEQ ID NO: 6            moltype = DNA   length = 21
FEATURE                 Location/Qualifiers
source                  1..21
                        mol_type = other DNA
                        organism = Synthetic construct
SEQUENCE: 6
ctgtgtgagt tcgccttcaa t                                            21

SEQ ID NO: 7            moltype = DNA   length = 21
FEATURE                 Location/Qualifiers
source                  1..21
                        mol_type = other DNA
                        organism = Synthetic construct
SEQUENCE: 7
cggcgcacag aggaagagaa t                                            21

SEQ ID NO: 8            moltype = DNA   length = 20
FEATURE                 Location/Qualifiers
source                  1..20
                        mol_type = other DNA
                        organism = Synthetic construct
SEQUENCE: 8
gttcacgttc tgcgtggtga                                              20

SEQ ID NO: 9            moltype = DNA   length = 20
FEATURE                 Location/Qualifiers
source                  1..20
                        mol_type = other DNA
                        organism = Synthetic construct
SEQUENCE: 9
aggagctcct gacactcgga                                              20

SEQ ID NO: 10           moltype = DNA   length = 20
FEATURE                 Location/Qualifiers
source                  1..20
                        mol_type = other DNA
                        organism = Synthetic construct
SEQUENCE: 10
atgaggagct gcggacgacg                                              20

SEQ ID NO: 11           moltype = DNA   length = 21
FEATURE                 Location/Qualifiers
source                  1..21
                        mol_type = other DNA
                        organism = Synthetic construct
SEQUENCE: 11
cagctcctca tcgtgttggt g                                            21

SEQ ID NO: 12           moltype = DNA   length = 22
FEATURE                 Location/Qualifiers
source                  1..22
                        mol_type = other DNA
                        organism = Synthetic construct
```

```
SEQUENCE: 12
gcacatacaa atggcctgtc tc                                              22

SEQ ID NO: 13          moltype = DNA  length = 19
FEATURE                Location/Qualifiers
source                 1..19
                       mol_type = other DNA
                       organism = Synthetic construct
SEQUENCE: 13
cacgcagaac gtgaacacc                                                  19

SEQ ID NO: 14          moltype = DNA  length = 21
FEATURE                Location/Qualifiers
source                 1..21
                       mol_type = other DNA
                       organism = Synthetic construct
SEQUENCE: 14
ggcagtagat aacgtgaggg a                                               21

SEQ ID NO: 15          moltype = DNA  length = 20
FEATURE                Location/Qualifiers
source                 1..20
                       mol_type = other DNA
                       organism = Synthetic construct
SEQUENCE: 15
tggatttgga cgcattggtc                                                 20

SEQ ID NO: 16          moltype = DNA  length = 21
FEATURE                Location/Qualifiers
source                 1..21
                       mol_type = other DNA
                       organism = Synthetic construct
SEQUENCE: 16
tttgcactgg tacgtgttga t                                               21
```